United States Patent
Inouye et al.

(10) Patent No.: US 9,469,845 B2
(45) Date of Patent: *Oct. 18, 2016

(54) MUTATED GENES FOR THE CATALYTIC PROTEIN OF OPLOPHORUS LUCIFERASE AND USE THEREOF

(71) Applicant: JNC Corporation, Tokyo (JP)

(72) Inventors: Satoshi Inouye, Kanagawa (JP); Junichi Sato, Kanagawa (JP)

(73) Assignee: JNC CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/157,930

(22) Filed: May 18, 2016

(65) Prior Publication Data

US 2016/0251634 A1 Sep. 1, 2016

Related U.S. Application Data

(62) Division of application No. 14/576,366, filed on Dec. 19, 2014.

(30) Foreign Application Priority Data

Dec. 26, 2013 (JP) ................................ 2013-268416

(51) Int. Cl.
*C12N 9/00* (2006.01)
*C12N 9/02* (2006.01)

(52) U.S. Cl.
CPC ............... *C12N 9/0069* (2013.01); *C12N 9/00* (2013.01); *C12Y 113/12007* (2013.01)

(58) Field of Classification Search
CPC ..................................................... C12N 9/00
See application file for complete search history.

(56) References Cited

U.S. PATENT DOCUMENTS

| | | | |
|---|---|---|---|
| 7,723,502 | B2 | 5/2010 | Coleman et al. |
| 8,557,970 | B2 | 10/2013 | Encell et al. |
| 8,809,529 | B2 | 8/2014 | Klaubert et al. |
| 2002/0102687 | A1 | 8/2002 | Inouye |
| 2014/0223590 | A1 | 8/2014 | Binkowski et al. |

FOREIGN PATENT DOCUMENTS

| | | |
|---|---|---|
| GB | 2425535 A | 11/2006 |
| GB | 2479847 A | 10/2011 |
| JP | 2002-320482 A | 11/2002 |
| JP | 4613441 B2 | 1/2011 |
| JP | 2012-525819 A | 10/2012 |
| WO | WO-2004042010 A2 | 5/2004 |
| WO | WO-2010/127368 A1 | 11/2010 |
| WO | WO-2011007314 A1 | 1/2011 |
| WO | WO-2011025980 A1 | 3/2011 |
| WO | WO-2012061529 A1 | 5/2012 |
| WO | WO-2012061530 A3 | 5/2012 |
| WO | WO-2012061530 A3 | 9/2012 |
| WO | WO-2012061530 A8 | 6/2013 |

OTHER PUBLICATIONS

Mary P. Hall, et al., "Engineered Luciferase Reporter from a Deep Sea Shrimp Utilizing a Novel Imidazopyrazinone Substrate," ACS Chemical Biology, 2012, 7, pp. 1848-1857.
Satoshi Inouye, et al., "Secretional luciferase of the luminous shrimp *Oplophorus gracilirostris*: cDNA cloning of a novel imidazopyrazinone luciferase[1]," FEBS Letters 481 (2000), pp. 19-25.
Satoshi Inouye, et al., "Overexpression, purification and characterization of the catalytic component of *Oplophorus* luciferase in the deep-sea shrimp, *Oplophorus* gracilirostris," Protein Expression and Purification 56 (2007), pp. 261-268.
Satoshi Inouye, et al., "C6-Deoxy coelenterazine analogues as an efficient substrate for glow luminescence reaction of nanoKAZ: The mutated catalytic 19 kDa component of *Oplophorus* luciferase," Biochemical and Biophysical Research Communications 437 (2013), pp. 23-28.
Osamu Shimomura, et al., "Properties and Reaction Mechanism of the Bioluminescence System of the Deep-Sea Shrimp *Oplophorus gracilorostris*", Biochemistry, vol. 17, No. 6, 1978, pp. 994-998.
GB Application No. 1403374.0—Search Report mailed Nov. 12, 2014.
Inouye, et al., "Soluble protein expression in *E. coli* cells using IgG-binding domain of protein A as a solubilizing partner in the cold induced system", Biochem. Biophys. Res. Commun., 2008, 376, pp. 448-453.
Inouye, et al., "The Use of *Renilla* Luciferase, *Oplophorus* Luciferase, and Apoaequorin as Bioluminescent Reporter Protein in the Presence of Coelenterazine Analogues as Substrate", Biochem. Biophys. Res. Commun., 1997, 233, pp. 349-353.
Nakamura, et al., "Efficient Bioluminescence of Bisdeoxycoelenterazine with the Luciferase of a Deep-Sea Shrimp *Oplophorus*", Tetrahedron Lett., 1997, vol. 38, No. 6, pp. 6405-6406.
Wu, et al., "Chemi- and bioluminescence of coelenterazine analogues with a conjugated group at the C-8 position", Tetrahedron Lett., 2001, 42, pp. 2997-3000.
Inouye, et al., "Expression, purification and luminescence properties of coelenterazine-utilizing luciferases from *Renilla*, *Oplophorus* and *Gaussia*: Comparison of substrate specificity for C2-modified coelenterazines", Protein Express. Purif., 2013, 88, pp. 150-156.
Shimomura, et al., "Recombinant aequorin and recombinant semi-synthetic aequorins," Biochem. J., 1990, vol. 270, pp. 309-312.
Shimumora, et al., "Semi-sysnthetic aequorin, An improved tool for the measurement of calcium ion concentration," Biochem. J., 1988, vol. 251, pp. 405-410.

(Continued)

*Primary Examiner* — Maryam Monshipouri
(74) *Attorney, Agent, or Firm* — Drinker Biddle & Reath LLP

(57) ABSTRACT

Secreted luciferases which are different from those known heretofore have been desired. The present invention provides a luciferase mutant comprising an amino acid sequence in which at least one amino acid selected from amino acids at the positions of 1 to 4 is deleted in the amino acid sequence of SEQ ID NO: 2.

15 Claims, 5 Drawing Sheets

(56) References Cited

OTHER PUBLICATIONS

Shimomura, et al., "Semi-synthetic aequorins with improved sensitivity to Ca2+ ions," Biochem. J., 1989, vol. 261, pp. 913-920.

Katsuhori Teranishi, "Luminescence of imidazo[1,2-a]pyrazin-3(7H)-one compounds," Bioorganic Chemistry, 2007, 35, pp. 82-111.

Inouye, et al., "Unconventional secretion of the mutated 19 kDa protein of Oplophorus luciferase (nanoKAZ) in mammalian cells", Biochemical and Biophysical Research Communications, Jul. 11, 2014, vol. 450, , No. 4, pp. 1313-1319.

GB Application 1422600.5—Search Report mailed Sep. 15, 2015.

GB Application No. 1418471.7—Search Report mailed Jun. 25, 2015.

GB Application No. 1406130.3—Search Report rhailed Nov. 11, 2014.

Inouye, et al., "Codon optimization of genes for efficient protein expression in mammalian cells by selection of only preferred human codons", Protein Expression and Purification, 2015, vol. 109, pp. 47-54.

Ngo, et al., "Computational Complexity, Protein Structure Prediction, and the Levinthal Paradox", The Protein Folding Problem and Tertiary Structure Prediction, 1994, Merz et al. (ed.), pp. 433 and 492-495.

MUTATED GENES FOR THE CATALYTIC PROTEIN OF OPLOPHORUS LUCIFERASE AND USE THEREOF

CROSS-REFERENCE TO RELATED PATENT APPLICATION

This is a Divisional of copending application Ser. No. 14/576,366, filed Dec. 19, 2014, which claims priority to Japanese Patent Application No. 2013-268416 filed Dec. 26, 2013

REFERENCE TO A SEQUENCE LISTING

The instant application contains a Sequence Listing which has been submitted in ASCII format via EFS-Web and is hereby incorporated by reference in its entirety. Said ASCII copy, created on May 13, 2016 is named 206313_0014_01_SL_ST25.txt and is 45,558 bytes in size.

TECHNICAL FIELD

The present invention relates to mutated genes for the catalytic protein of *Oplophorus* luciferase, use thereof and so on.

BACKGROUND OF INVENTION

Bioluminescence is a phenomenon based on a chemical reaction in vivo, which is called a luciferin (a luminescence substrate)-luciferase (an enzyme that catalyzes the luminescence reaction) reaction. Numerous studies of the identification of luciferins or luciferases and the elucidation of the luminescence mechanism in a molecular level have been performed for a long time in the country and overseas. In bioluminescent marine organisms, *Oplophorus gracilirostris* luciferase from the deep-sea shrimp is an extracellularly secreted luciferase (Non-Patent Document 1).

*Oplophorus* luciferase is a 106 kDa protein composed of a protein with a molecular weight of 35 kDa and a protein with a molecular weight of 19 kDa. The domain that catalyzes the luminescence is found to be 19 kDa protein. *Oplophorus* luciferase uses coelenterazine as a luminescence substrate and is classified as a coelenterazine-type luciferase (Patent Document 1, Non-Patent Document 2). *Oplophorus* luciferase is different from other coelenterazine-type luciferases in broad substrate specificity and uses coelenterazine analogues as a suitable substrate as well as coelenterazine (Non-Patent Document 2). When the gene for the 19 kDa protein is expressed in *Escherichia coli* (*E. coli*) at ambient and lower temperatures, the protein is expressed mostly as an insoluble protein (Non-Patent Document 3). When the 19 kDa protein was expressed as a fusion protein to ZZ domain from protein A in a low temperature expression system, the fused protein could be expressed as a soluble protein (Non-Patent Document 4). It is reported that when the 19 kDa protein was expressed in animal cultured cells, the expressed protein was hardly secretion outside of cells (Non-Patent Document 2).

Recently, it is reported that the mutated 19 kDa protein having catalytic activity of luminescence was prepared by mutating the 16 amino acids of the 19 kDa protein and showed higher luminescence activity than native 19 kDa protein, and was secreted into an extracellular medium (Patent Document 2, Non-Patent Documents 4 and 5). It is also reported that coelenterazine derivatives displayed higher activity than native coelenterazine used as a substrate (Non-Patent Documents 4 and 5).

In the luminescence reaction system using coelenterazine as a substrate, the luminescence reaction of luciferase proceeds only by a substrate and molecular oxygen. From this reason, a coelenterazine-type luciferase gene is used widely as a reporter assay in an animal cultured cell system at present. *Renilla* luciferase having 311 amino acids is used for a reporter assay inside of cells. For an extracellular reporter assay, the secreted *Gaussia* luciferase which is a secretory luciferase with a secretory signal peptide sequence of 17 amino acids and having 168 amino acids is used.

[Related Art Documents]
[Patent Documents]
[Patent Document 1] Japanese Laid-Open Patent Publication (Tokkai) No. 2002-320482
[Patent Document 2] Japanese National Publication (Tokuhyo) No. 2012-525819
[Non-Patent Documents]
[Non-Patent Document 1] O. Shimomura et al. (1978) Biochemistry 17: 994-998.
[Non-Patent Document 2] S. Inouye et al. (2000) FEBS Lett. 481: 19-25.
[Non-Patent Document 3] S. Inouye & S. Sasaki (2007) Protein Express. Purif. 56: 261-268.
[Non-Patent Document 4] M. P. Hall et al. (2012) ACS Chem Biol. 7: 1848-1857.
[Non-Patent Document 5] S. Inouye et al. (2013) Biochem. Biophys. Res. Commun. 437: 23-28.

DISCLOSURE OF THE INVENTION

Problems to be solved by the Invention

Under the foregoing circumstances, a novel luciferase that is distinct from conventional luciferase has been desired.

Means for Solving the Problem

The present inventors have made extensive investigations to solve the problem above, and examined the reported 19 kDa protein mutants which catalyze the luminescence reaction. As a result, the inventors have a newly constructed luciferase mutant or the like, which are secreted extracellularly in the absence of any secretory signal peptide sequences, when the mutant is expressed in animal cultured cells. The present invention has thus been accomplished.

More specifically, the present invention provides the following luciferase mutants, polynucleotides, recombinant vectors, a method of producing luciferase mutants, kits, a method for performing a luminescence reaction, and so on.

[1] A luciferase mutant selected from (a) to (d) below:
(a) a luciferase mutant comprising an amino acid sequence in which at least one amino acid selected from the 1st to 4th amino acids is deleted in the amino acid sequence of SEQ ID NO: 2;
(b) a luciferase mutant comprising an amino acid sequence in which at least one amino acid selected from amino acids at the positions of 1 to 4 is deleted in the amino acid sequence of SEQ ID NO: 2 and an amino acid sequence excluding the amino acids at the positions of 1 to 4 is an amino acid sequence in which 1 to 17 amino acids are deleted, substituted, inserted and/or added in the amino acid sequence at the positions of 5 to 169 of SEQ ID NO: 2, and having a luciferase activity;
(c) a luciferase mutant comprising an amino acid sequence in which at least one amino acid selected from amino acids at the positions of 1 to 4 is deleted in the amino acid sequence of SEQ ID NO: 2 and an amino acid sequence excluding the amino acids at the positions of 1 to 4 has at least 90% identity to the amino acid sequence at the positions of 5 to 169 of SEQ ID NO: 2, and having a luciferase activity; and, p (d) a luciferase mutant comprising an amino acid sequence in which at least one amino acid selected from amino acids at the positions of 1 to 4 is deleted in the amino acid sequence of SEQ ID NO: 2 and an amino acid sequence excluding the amino acids at the positions of 1 to 4 is encoded by a polynucleotide which hybridizes under stringent conditions to a polynucleotide consisting of a nucleotide sequence complementary to a nucleotide sequence encoding the amino acid sequence at the positions of 5 to 169 of SEQ ID NO: 2, and having a luciferase activity.

[2] The luciferase mutant according to [1] above, wherein the luciferase mutants defined in (b) to (d) above are mutants defined in (b-1) to (d-1) below:

(b-1) a luciferase mutant comprising an amino acid sequence in which at least one amino acid selected from amino acids at the positions of 1 to 4 is deleted in the amino acid sequence of SEQ ID NO: 2 and an amino acid sequence excluding the amino acids at the positions of 1 to 4 is an amino acid sequence in which 1 to 9 amino acids are deleted, substituted, inserted and/or added in the amino acid sequence at the positions of 5 to 169 of SEQ ID NO: 2, and having a luciferase activity;

(c-1) a luciferase mutant comprising an amino acid sequence in which at least one amino acid selected from amino acids at the positions of 1 to 4 is deleted in the amino acid sequence of SEQ ID NO: 2 and an amino acid sequence excluding the amino acids at the positions of 1 to 4 has at least 95% identity to the amino acid sequence at the positions of 5 to 169 of SEQ ID NO: 2, and having a luciferase activity; and, (d-1) a luciferase mutant comprising an amino acid sequence in which at least one amino acid selected from amino acids at the positions of 1 to 4 is deleted in the amino acid sequence SEQ ID NO: 2 and an amino acid sequence excluding the amino acids at the positions of 1 to 4 is encoded by a polynucleotide which hybridizes under high stringent conditions to a polynucleotide consisting of a nucleotide sequence complementary to a nucleotide sequence encoding the amino acid sequence at the positions of 5 to 169 of SEQ ID NO: 2, and having a luciferase activity.

[3] The luciferase mutant according to [1] above, wherein the luciferase mutant of (a) above comprises the amino acid sequence selected from SEQ ID NO: 4, SEQ ID NO: 6, SEQ ID NO: 8 and SEQ ID NO: 10.

[4] A polynucleotide comprising a polynucleotide encoding the luciferase mutant according to any one of [1] to [3] above.

[5] A recombinant vector comprising the polynucleotide according to [4] above.

[6] A transformant transformed with the recombinant vector according to [5] above.

[7] A method of producing the luciferase mutant according to any one of [1] to [3] above, which comprises the steps of culturing the transformant of [6] above and producing the luciferase mutant according to any one of [1] to [3] above.

[8] A kit comprising at least one selected from the luciferase mutant according to any one of [1] to [3] above, the polynucleotide according to [4] above, the recombinant vector according to [5] above and the transformant according to [6] above.

[9] The kit according to [8] above, further comprising a luciferin.

[10] The kit according to [9] above, wherein the luciferin is coelenterazines.

[11] The kit according to [10] above, wherein the coelenterazines are bis-coelenterazine or 6h-f-coelenterazine.

[12] A method for performing a luminescence reaction, which comprises contacting the luciferase mutant according to any one of [1] to [3] above with a luciferin.

[13] The method according to [12] above, wherein the luciferin is coelenterazines.

[14] The method according to [13] above, wherein the coelenterazines are bis-coelenterazine or 6h-f-coelenterazine.

[15] A method for assaying an activity of a sequence associated with the regulation of a promoter, which comprises using the polynucleotide according to [4] above as a reporter gene and contacting a luciferase mutant encoded by the reporter gene with a luciferin.

[16] The method according to [15] above, wherein the luciferin is coelenteazines.

[17] The method according to [16] above, wherein the coelenterazines are bis-coelenterazine or 6h-f-coelenterazine.

[18] A method of visualizing a luminescence reaction, which comprises contacting the luciferase mutant according to any one of [1] to [3] above with a luciferin.

[19] The method according to [18] above, wherein the luciferin is coelenterazines.

[20] The method according to [19] above, wherein the coelenterazines are h-coelenterazine or f-coelenterazine.

Effects of the Invention

The present invention provides secreted luciferase mutants that are distinct from the known mutants. In a preferred embodiment of the invention, the luciferase mutants are novel luciferases which are secreted extracellularly from the endoplasmic reticulum but not via the trans-Golgi network when the proteins are expressed in animal cells, and can be used to visualize the secretory pathway.

MODE FOR CARRYING OUT THE INVENTION

Figure 1:
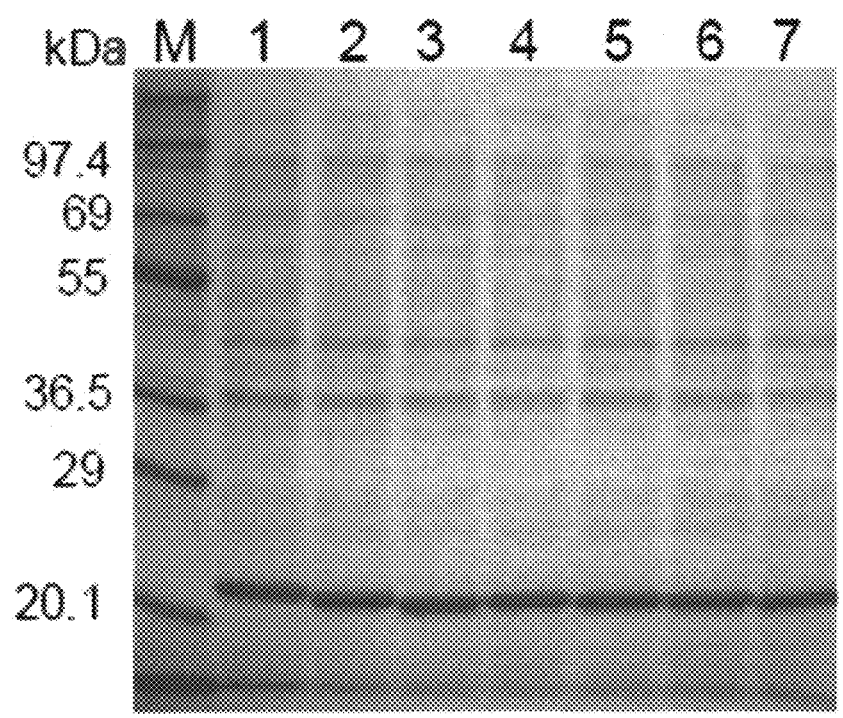
FIG. 1 shows the results of SDS-PAGE analysis of the crude enzyme solution (crude extracts) of *E. coli* in which the amino-terminal deleted nanoKAZ was expressed using a pColdII vector.

The present invention will be described below in detail.
1. Luciferase Mutants of the Invention The term luciferase mutant of the present invention refers to a mutant of the protein with a molecular weight of 19 kDa of *Oplophorus* luciferase. Specifically, the luciferase mutant of the present invention is intended to mean a luciferase mutant having substantially the same activity as the luciferase mutant comprising an amino acid sequence in which at least one amino acid selected from amino acids at the positions of 1 to 4 is deleted in the amino acid sequence of SEQ ID NO: 2.

The term substantially the same activity is intended to mean at least one activity selected from luciferase activity, activity for extracellular secretion when expressed in animal cells in the absence of any secretory signal peptide sequences, and so on.

The term "luciferase activity" is intended to mean the activity for catalyzing the luminescence reaction using a luciferin (e.g., coelenterazines) which serves as a substrate, namely, the reaction in which luciferin (e.g., coelenterazines) is oxidized with molecular oxygen to produce oxyluciferin in its excited state. The excited state of oxyluciferin produced emits visible light and converts to the ground state of oxyluciferin.

Luminescence activity can be determined by the method described in, e.g., Inouye, S. & Shimotnura, O. (1977) Biochem. Biophys. Res. Commun. 233, 349-353. Specifically, the luciferase mutant of the present invention is mixed with a luciferin to start the luminescence reaction, and the activity of catalyzing luminescence reaction can be determined using a luminometer. Commercially available luminometers, e.g., Luminescencer-PSN AB2200 (manufactured by Atto Corp.) or Centro 960 luminometer (manufactured by Berthold Inc.) may be used as luminometers.

The luciferin used in the present invention may be any luciferin as far as it serves as a substrate for the luciferase mutants of the present invention. Specifically, the luciferin used in the present invention includes coelenterazines containing the imidazopyrazinone ring as the backbone.

The term coelenterazines are used to mean coelenterazine (also referred to as "native coelenterazine") or its analogues. Coelenterazine analogues include, for example, bis-coelenterazine, 6hf-coelenterazine, deoxyfuran-coelenterazine (furimazine), h-coelenterazine, hcp-coelenterazine, cp-coelenterazine, f-coelenterazine, fcp-coelenterazine, n-coelenterazine, MeO-coelenterazine, e-coelenterazine, cl-coelenterazine, ch-coelenterazine, 3iso-coelenterazine, 3meo-coelenterazine, cf3-coelenterazine, i-coelenterazine, et-coelenterazine, me-coelenterazine, 3me-coelenterazine, αmeh-coelenterazine, 8-(1-naphthyl)-coelenterazine, 8-(2-naphthyl)-coelenterazine, 8-(2-thienyl)-coelenterazine, 6,8-di-(2-thienyl)-coelenterazine, 8-(4-hydroxyphenyl)-coelenterazine, 8-(2-benzothienyl)-coelenterazine, 8-(b-styryl)-coelenterazine, 8-phenyl-coelenterazine, 6-deoxycoelenterazine, 8-(3-thienyl)-coelenterazine, and 8-(3-benzo[b]thienyl)-coelenterazine. Of these coelenterazines, bis-coelenterazine or 6h-f-coelenterazine is particularly preferred in some embodiments of the present invention. In some other embodiments of the present invention, h-coelenterazine or f-coelenterazine is particularly preferred.

These coelenterazines could be synthesized by publicly known methods or may also be commercially available.

The coelenterazines could be synthesized by the methods described in, e.g., Shimomura et al. (1988) Biochem. J. 251, 405-410, Shimomura et al. (1989) Biochem. J. 261, 913-920, Shimomura et al. (1990) Biochem. J. 270, 309-312, Tetrahedron Lett. 38: 6405-6406, WO 2010/090319, Inouye et al. (2010) Anal. Biochem. 407, 247-252 or Inouye et al. (2013) Biocchem. Biophys. Res. Commun. 437, 23-28, or respective modifications thereof. Furimazine may be produced by the method described in Hall et al. (2012) ACS Chem. Biol. 16; 848-1857.

The coelenterazines which are commercially available include, for example, coelenterazine, cf3-coelenterazine and h-coelenterazine manufactured by JNC Corp.; hcp-coelenterazine, cp-coelenterazine, f-coelenterazine, fcp-coelenterazine and n-coelenterazine manufactured by Biotium Inc.; and bis-coelenterazine manufactured by Prolume Ltd. and coelenterazine, furimazine and h-coelenterazine manufactured by Promega Corp.

The "luminescence activity using a luciferin as a substrate" refers to luminescence activity using preferably coelenterazines as a substrate. In a preferred embodiment of the invention, the "luminescence activity using coelenterazines as a substrate" is the luminescence activity in which bis-coelenterazine or 6h-f-coelenterazine serves as the substrate. In another preferred embodiment of the invention, the "luminescence activity using coelenterazines as a substrate" is the luminescence activity in which h-coelenterazine or f-coelenterazine serves as the substrate.

The "activity for extracellular secretion (secreting extracellularly) when expressed in animal cells in the absence of any secretory signal peptide sequences" is intended to mean that when the protein is expressed in animal cells, the expressed protein is secreted extracellularly from the endoplasmic reticulum but not via the trans-Golgi network, despite having no secretory signal peptide. The "extracellular secretion (secreting extracellularly)" refers specifically to extracellular secretion of the protein in an amount (by weight) of 5% or more, 10% or more, or 20% or more of the expressed protein. Specific examples of the "animal cells" are those later described. The "secretory signal peptide" is intended to mean a signal for secretion, excluding the region in which the secretion information of nanoKAZ is carried, specifically excluding the region of amino acids at the positions of 1 to 4 from the amino terminus.

The "luciferase mutant having substantially the same activity as the luciferase mutant comprising an amino acid sequence in which at least one amino acid selected from amino acids at the positions of 1 to 4 is deleted in the amino acid sequence of SEQ ID NO: 2" includes, for example, a luciferase mutant selected from (a) to (d) described below.

(a) a luciferase mutant comprising an amino acid sequence in which at least one amino acid selected from the 1st to 4th amino acids is deleted in the amino acid sequence of SEQ ID NO: 2;

(b) a luciferase mutant comprising an amino acid sequence in which at least one amino acid selected from amino acids at the positions of 1 to 4 is deleted in the amino acid sequence of SEQ ID NO: 2 and an amino acid sequence excluding the amino acids at the positions of 1 to 4 is an amino acid sequence in which 1 to 17 amino acids are deleted, substituted, inserted and/or added in the amino acid sequence at the positions of 5 to 169 of SEQ ID NO: 2, and having a luciferase activity;

(c) a luciferase mutant comprising an amino acid sequence in which at least one amino acid selected from amino acids at the positions of 1 to 4 is deleted in the amino acid sequence of SEQ ID NO: 2 and an amino acid sequence excluding the amino acids at the positions of 1 to 4 has at least 90% identity to the amino acid sequence at the positions of 5 to 169 of SEQ ID NO: 2, and having a luciferase activity; and, (d) a luciferase mutant comprising an amino acid sequence in which at least one amino acid selected from amino acids at the positions of 1 to 4 is deleted in the amino acid sequence of SEQ ID NO: 2 and an amino acid sequence excluding the amino acids at the positions of 1 to 4 is encoded by a polynucleotide which hybridizes under stringent conditions to a polynucleotide consisting of a nucleotide sequence complementary to a nucleotide sequence encoding the amino acid sequence at the positions of 5 to 169 of SEQ ID NO: 2, and having a luciferase activity.

In (a) to (d) described above, the term "at least one amino acid selected from amino acids at the positions of 1 to 4 is deleted in the amino acid sequence of SEQ ID NO: 2" is intended to mean a deletion of at least one amino acid residue at the positions of 1 to 4 in the amino acid sequence of SEQ ID NO: 2. Preferably, the amino acid at the position of 1, all amino acids at the positions of 1 and 2, all amino acids at the positions of 1 to 3 or all amino acids at the positions of 1 to 4 are deleted.

Specifically, "at least one" in "at least one amino acid is deleted" refers to 1, 2, 3 or 4, preferably 1 or 2, and more preferably 1.

In (b) to (d) described above, the "amino acid sequence excluding the amino acids at the positions of 1 to 4" is intended to mean an amino acid sequence corresponding to the amino acid sequence at the positions of 5 to 169 of SEQ ID NO: 2 prior to the mutation, in each of the amino acid sequences in the luciferase mutants defined in (b) to (d) described above.

In (b) above, the term "1 to 17 amino acids are deleted, substituted, inserted and/or added" is intended to mean that the deletion, substitution, insertion and/or addition of 1 to 17 amino acid residues occur at an optional position(s) in the same sequence and at 1 to 17 positions in the amino acid sequence.

The range of "1 to 17" in the "1 to 17 amino acids are deleted, substituted, inserted and/or added" described above is, for example, 1 to 17, 1 to 16, 1 to 15, 1 to 14, 1 to 13, 1 to 12, 1 to 11, 1 to 10, 1 to 9, 1 to 8, 1 to 7, 1 to 6 (1 to several), 1 to 5, 1 to 4, 1 to 3, 1 to 2 and 1. In general, the less the number of amino acids deleted, substituted, inserted and/or added, the more preferred. Such proteins may be produced by site-directed mutagenesis described in J. Sambrook, E. F. Fritsch & T. Maniatis (Ed.), Molecular cloning, a laboratory manual (4th edition), Cold Spring Harbor Press, Cold Spring Harbor, N.Y. (2012); Ausbel F. M. et al., Current Protocols in Molecular Biology, Supplement 1-38, John Wiley and Sons (1987-1997); Nuc. Acids. Res., 10, 6487 (1982); Proc. Natl. Acad. Sci. USA, 79, 6409 (1982); Gene, 34, 315 (1985); Nuc. Acids. Res., 13, 4431 (1985); Proc. Natl. Acad. Sci. USA, 82, 488 (1985), etc.

The position(s) of the amino acid(s) which is/are substituted in the amino acid sequence at the positions of 5 to 169 of SEQ ID NO: 2 are not particularly limited so long as it is other than at the positions of 11, 18, 27, 33, 43, 68, 72, 75, 90, 115, 124 and 166, and include one or more position(s) selected from the group consisting of the positions of 13, 14, 15, 25, 30, 36, 70, 83, 106, 128, 153, 156, 157, 159, 162, 163 and 169. In particular, the substitution positions can be at least (one or more) position(s) selected from the group consisting of the positions of 13, 14, 153, 159, 163 and 169.

Examples of amino acid residues which are mutually substitutable are given below. Amino acid residues in the same group are mutually substitutable.

Group A: leucine, isoleucine, norleucine, valine, norvaline, alanine, 2-aminobutanoic acid, methionine, o-methylserine, t-butylglycine, t-butylalanine and cyclohexylalanine;

Group B: aspartic acid, glutamic acid, isoaspartic acid, isoglutamic acid, 2-aminoadipic acid and 2-aminosuberic acid;

Group C: asparagine and glutamine;

Group D: lysine, arginine, ornithine, 2,4-diaminobutanoic acid and 2,3-diaminopropionic acid;

Group E: proline, 3-hydroxyproline and 4-hydroxyproline;

Group F: serine, threonine and homoserine; and,

Group G: phenylalanine and tyrosine.

In (c) described above, the range of "at least 90%" in the "amino acid sequence having at least 90% identity" is, for example, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more. In general, the numerical value of the identity described above is more preferable as the number becomes larger. The identity of amino acid sequences or nucleotide sequences can be determined using sequencing programs such as BLAST (see, e.g., Altzchul, S. F. et al., J. Mol. Biol., 215, 403 (1990)). When BLAST is used, the default parameters for the respective programs are employed.

In (d) described above, the "polynucleotide which hybridizes under stringent conditions" is intended to mean a polynucleotide (e.g., DNA) which is obtained by, for example, colony hybridization, plaque hybridization or Southern hybridization using as a probe all or part of the polynucleotide consisting of a nucleotide sequence complementary to the nucleotide sequence encoding the amino acid sequence at the positions of 5 to 169 of SEQ ID NO: 2. Specific examples include polynucleotides which can be identified by performing hybridization at 65° C. in the presence of 0.7 to 1.0 mol/L NaCl using a filter on which the polynucleotide from a colony or plaque is immobilized, then washing the filter at 65° C. with an SSC (saline-sodium citrate) solution having a concentration of 0.1 to 2 times (1× SSC solution is composed of 150 mmol/L sodium chloride and 15 mmol/L sodium citrate).

Hybridization may be performed in accordance with modifications of the methods described in laboratory manuals, e.g., J. Sambrook, E. F. Fritsch & T. Maniatis (Ed.), Molecular Cloning, A Laboratory Manual (4th edition), Cold Spring Harbor Press, Cold Spring Harbor, N.Y. (2012), Ausbel F. M. et al., Current Protocols in Molecular Biology, Supplement 1-38, John Wiley and Sons (1987-1997), Glover D. M. and Hames B. D., DNA Cloning 1: Core Techniques, A practical Approach, Second Edition, Oxford University Press (1995), etc.

The "stringent conditions" may be any of low stringent conditions, moderate stringent conditions or high stringent conditions. The "low-stringent conditions" are, for example, conditions of 5× SSC, 5× Denhart's solution, 0.5% (w/v) SDS, 50% (v/v) formamide and 32° C. The "moderate stringent conditions" are, for example, conditions of 5× SSC, 5× Denhart's solution, 0.5% (w/v) SDS, 50% (v/v) formamide and 42° C. The "high-stringent conditions" are, for example, 5× SSC, 5× Denhart's solution, 0.5% (w/v)

SDS, 50% (v/v) formamide and 50° C. The more stringent the conditions are, the higher the complementarity required for double-strand formation. Specifically, under these conditions, for example, a polynucleotide (e.g., DNA) of higher homology is expected to be obtained efficiently as the temperature becomes higher, although multiple factors are involved in hybridization stringency, including temperature, probe concentration, probe length, ionic strength, time, base concentration, etc. One skilled in the art may achieve a similar stringency by appropriately choosing these factors.

When commercially available kits are used for the hybridization, for example, Alkphos Direct Labeling Reagents (manufactured by GE Healthcare Inc.) can be used. In this case, according to the protocol attached, a membrane is incubated with a labeled probe overnight, the membrane is washed with a primary wash buffer containing 0.1% (w/v) SDS under conditions at 55° C. and then the hybridized DNA can be detected.

Other hybridizable polynucleotides include, as calculated by a sequencing program such as BLAST or the like using the default parameters, DNAs having the identity of approximately 60% or more, 65% or more, 70% or more, 75% or more, 80% or more, 85% or more, 88% or more, 90% or more, 92% or more, 95% or more, 97% or more, 98% or more, 99% or more, 99.3% or more, 99.5% or more, 99.7% or more, 99.8% or more, or 99.9% or more, to the polynucleotide consisting of the nucleotide sequence of SEQ ID NO: 2. The identity of nucleotide sequences can be determined using the method described above.

In a preferred embodiment of the invention, the luciferase mutant is a luciferase mutant comprising the amino acid sequence of SEQ ID NO: 4, SEQ ID NO: 6, SEQ ID NO: 8 or SEQ ID NO: 10, more preferably, a luciferase mutant comprising the amino acid sequence of SEQ ID NO: 4, SEQ ID NO: 6 or SEQ ID NO: 8, and most preferably, a luciferase mutant comprising the amino acid sequence of SEQ ID NO: 4.

The luciferase mutant of the present invention may further contain an additional peptide sequence at the N terminus and/or C terminus, preferably at the N terminus. The additional peptide sequence is at least one peptide sequence selected from the group consisting of a peptide sequence for purification, a peptide sequence for expressing the luciferase mutant of the present invention as a soluble protein and an epitope sequence capable of recognizing an antibody. The additional peptide sequence is preferably a peptide sequence for purification. In another preferred embodiment of the invention, the additional peptide sequence is at least one sequence selected from the group consisting of a peptide sequence for purification and a peptide sequence for expressing the luciferase mutant of the present invention as a soluble protein.

Peptide sequences employed in the art may be used as the peptide sequence for purification. The peptide sequence for purification includes, for example, a histidine tag sequence with a consecutive amino acid sequence of at least 4 histidine residues and preferably at least 6 residues, an amino acid sequence with a binding domain of glutathione S-transferase into glutathione, the amino acid sequence of Protein A, etc.

The peptide used to express the luciferase mutant of the present invention as a soluble protein includes, for example, polypeptides represented by formula $(Z)_n$. The amino acid sequences for the polypeptides represented by formula $(Z)_n$ and the nucleic acid sequences encoding the same are described in, e.g., JPA KOKAI No. 2008-99669.

Peptide sequences used in the art can be used as the epitope sequence capable of recognizing an antibody.

In some embodiments of the present invention, the additional peptide sequence in the luciferase mutant does not carry a secretory signal peptide sequence. The "secretory signal peptide sequence" includes a secretory peptide sequence of *Gaussia* luciferase, or the like.

The method for acquiring the luciferase mutant of the invention is not particularly limited. The luciferase mutant of the invention may be a protein synthesized by chemical synthesis, or a recombinant protein produced by a genetic engineering technique. When the luciferase mutant of the invention is to be chemically synthesized, synthesis may be carried out by, for example, the Fmoc (fluorenylmethyloxycarbonyl) method or the tBoc (t-butyloxycarbonyl) method. In addition, peptide synthesizers available from Advanced Chem Tech, PerkinElmer, Pharmacia, Protein Technology Instrument, Synthecell-Vega, PerSeptive, Shimadzu Corporation, etc. may also be used for chemical synthesis. When the luciferase mutant of the invention is to be produced by a genetic engineering technique, the mutant may be produced by a conventional genetic recombination technique. More specifically, the luciferase mutant of the invention may be produced by inserting a polynucleotide (e.g., a DNA) encoding the luciferase mutant of the invention into a suitable expression system. The polynucleotide encoding the luciferase mutant of the invention, expression of the luciferase mutant of the invention in an expression system or the like will be later described.

2. Polynucleotide of the Invention

The present invention also provides a polynucleotide comprising a polynucleotide encoding the luciferase mutant of the invention described above. The polynucleotide of the invention may be any polynucleotide so long as it has a nucleotide sequence encoding the luciferase mutant of the invention, although a DNA is preferred. Examples of the DNA include genomic DNA, genomic DNA library, cellular or tissue cDNA, cellular or tissue cDNA library, synthetic DNA, etc. Vectors used in the libraries are not particularly limited and may be any of bacteriophages, plasmids, cosmids, phagemids, etc. Also, these vectors may be amplified directly by a Reverse Transcription Polymerase Chain Reaction (hereinafter abbreviated as RT-PCR) using the total RNA or mRNA fraction prepared from the cell or tissue described above.

The polynucleotide of the invention includes the following polynucleotides (i) to (iv).

(i) A polynucleotide comprising a polynucleotide encoding the luciferase mutant described in (a) above;

(ii) A polynucleotide comprising a polynucleotide encoding the luciferase mutant described in (b) above;

(iii) A polynucleotide comprising a polynucleotide encoding the luciferase mutant described in (c) above; and (iv) A polynucleotide comprising a polynucleotide encoding the luciferase mutant described in (d) above.

A polynucleotide encoding a protein having a given amino acid sequence, in which one or more amino acids are substituted in the amino acid sequence, can be obtained by using a site-specific mutagenesis technique (see, e.g., Gotoh, T. et al., Gene 152, 271-275 (1995), Zoller, M. J., and Smith, M., Methods Enzymol. 100, 468-500 (1983), Kramer, W. et al., Nucleic Acids Res. 12, 9441-9456 (1984), Kramer W, and Fritz H. J., Methods. Enzymol. 154, 350-367 (1987), Kunkel, T. A., Proc. Natl. Acad. Sci. USA. 82, 488-492 (1985), Kunkel, Methods Enzymol. 85, 2763-2766 (1988);

etc.), the methods using amber mutation (see, e.g., the gapped duplex method, Nucleic Acids Res., 12, 9441-9456 (1984), etc.), etc.

Alternatively, mutations may also be introduced into the polynucleotide by PCR (cf, e.g., Ho S. N. et al., Gene, 77, 51 (1989), etc.) using a pair of primers bearing on the respective 5' ends a sequence in which the targeted mutation (deletion, addition, substitution and/or insertion) has been introduced.

Also, a polynucleotide encoding a partial fragment of protein, which is one type of the deletion mutant, can be obtained using as the primers an oligonucleotide having a sequence which matches the nucleotide sequence at the 5' end of the region encoding the partial fragment to be produced in the polynucleotide encoding the target protein and an oligonucleotide having a sequence complementary to the nucleotide sequence at the 3' end thereof, and performing PCR in which the polynucleotide encoding the target protein is used as a template.

The polynucleotide of the present invention includes preferably a polynucleotide comprising a polynucleotide encoding the luciferase mutant comprising the amino acid sequence of SEQ ID NO: 4, SEQ ID NO: 6, SEQ ID NO: 8 or SEQ ID NO: 10, more preferably, a polynucleotide comprising a polynucleotide encoding the luciferase mutant comprising the amino acid sequence of SEQ ID NO: 4, SEQ ID NO: 6 or SEQ ID NO: 8, and most preferably, a polynucleotide comprising a polynucleotide encoding the luciferase mutant comprising the amino acid sequence of SEQ ID NO: 4.

The polynucleotide encoding the luciferase mutant comprising the amino acid sequence of SEQ ID NO: 2 includes a polynucleotide comprising the nucleotide sequence of SEQ ID NO: 1. The polynucleotide encoding the luciferase mutant comprising the amino acid sequence of SEQ ID NO: 4 includes a polynucleotide comprising the nucleotide sequence of SEQ ID NO: 3. The polynucleotide encoding the luciferase mutant comprising the amino acid sequence of SEQ ID NO: 6 includes a polynucleotide comprising the nucleotide sequence of SEQ ID NO: 5. The polynucleotide encoding the luciferase mutant comprising the amino acid sequence of SEQ ID NO: 8 includes a polynucleotide comprising the nucleotide sequence of SEQ ID NO: 7. The polynucleotide encoding the luciferase mutant comprising the amino acid sequence of SEQ ID NO: 10 includes a polynucleotide comprising the nucleotide sequence of SEQ ID NO: 9.

In some embodiments of the present invention, the polynucleotide is preferably a polynucleotide comprising a polynucleotide consisting of the nucleotide sequence of SEQ ID NO: 3, SEQ ID NO: 5, SEQ ID NO: 7 or SEQ ID NO: 9, more preferably, a polynucleotide comprising a polynucleotide consisting of the nucleotide sequence of SEQ ID NO: 3, SEQ ID NO: 5 or SEQ ID NO: 7, and most preferably, a polynucleotide comprising a polynucleotide consisting of the nucleotide sequence of SEQ ID NO: 3.

The polynucleotide of the present invention may further contain a polynucleotide encoding an additional peptide sequence at the 5' end and/or 3' end, preferably at the 5' end. The polynucleotide encoding the additional peptide sequence includes a polynucleotide encoding at least one peptide sequence selected from the group consisting of a peptide sequence for purification, a peptide sequence for expressing the luciferase mutant of the present invention as a soluble protein, an epitope sequence capable of recognizing an antibody, and the like.

Polynucleotides comprising nucleotide sequences encoding the peptide sequence for purification employed in the art can be used as the polynucleotide encoding the peptide sequence for purification. Examples of the peptide sequence for purification include those as described above.

The polynucleotide encoding the peptide sequence used to express the luciferase mutant of the present invention as a soluble protein includes, for example, polypeptides represented by formula $(Z)_n$. The amino acid sequences for the polypeptides represented by formula $(Z)_n$ and the nucleic acid sequences encoding the same are those as described above.

Polynucleotides comprising nucleotide sequences encoding the epitope sequence capable of recognizing antibodies which are used in the art can be used as the polynucleotide encoding the antibody-recognizing epitope sequence.

In some embodiments of the present invention, a polynucleotide as the polynucleotide encoding the additional peptide sequence does not include polynucleotides encoding a secretory signal peptide sequence. The "secretory signal peptide sequence" includes those as described above, and the like.

3. Recombinant Vector and Transformant of the Invention

The present invention further provides recombinant vectors and transformants comprising the polynucleotides of the present invention described above.

Preparation of Recombinant Vector

The recombinant vector of the invention can be obtained by ligating (inserting) the polynucleotide (DNA) of the invention to (into) an appropriate vector. More specifically, the recombinant vector can be obtained by digesting the purified polynucleotide (DNA) with a suitable restriction enzyme, then inserting into a suitable vector at the restriction enzyme site or multiple-cloning site, and ligating to the vector. The vector for inserting the polynucleotide of the invention is not particularly limited as long as it is replicable in a host, and includes plasmids, bacteriophages, animal viruses, etc. Examples of plasmids include plasmids from *E. coli* (e.g., pBR322, pBR325, pUC118, pUC119, etc.), plasmids from *Bacillus subtilis* (e.g., pUB110, pTP5, etc.) and plasmids from yeast (e.g., YEp13, YEp24, YCp50, etc.). Examples of bacteriophages include, e.g., λ phage. Examples of animal viruses include retroviruses, vaccinia viruses and insect viruses (e.g., baculoviruses). In addition, a pCold I vector, a pCold II vector, a pCold III vector and a pCold IV vector (all manufactured by Takara Bio Inc.), a pcDNA3 vector, a PICZa vector (manufactured by Invitrogen Inc.) and the like may also be suitably used.

The polynucleotide of the present invention is generally ligated in an expressible manner downstream of a promoter in a suitable vector. When the host used for transformation is an animal cell, the promoter is preferably an SV40-derived promoter, retrovirus promoter, metallothionein promoter, heat shock promoter, cytomegalovirus promoter, SRα promoter, and so on. When the host is a bacterium of the genus *Escherichia*, Trp promoter, T7 promoter, lac promoter, recA promoter, λPL promoter, lpp promoter, etc. are preferred. When the host is a bacterium of the genus *Bacillus*, SPO1 promoter, SPO2 promoter, penP promoter, etc. are preferred. When the host is yeast, PHO5 promoter, PGK promoter, GAP promoter, ADH1 promoter, GAL promoter, etc. are preferred. When the host is an insect cell, polyhedrin promoter, P10 promoter, etc. are preferred.

A low-temperature expression-inducible promoter may also be suitably used. Examples of the low-temperature expression-inducible promoter include promoter sequences for cold shock genes. The cold shock gene includes, for example, *E. coli* cold shock genes (e.g., cspA, cspB, cspG, cspI and csdA), *Bacillus caldolyticus* cold shock genes (e.g., Bc-Csp), *Salmonella enterica* cold shock genes (e.g., cspE) and *Erwinia carotovora* cold shock genes (e.g., cspG). Among others, cspA promoter, cspB promoter, cspG promoter, cspI promoter, csdA promoter and the like can be advantageously used as the low-temperature expression-inducible promoter.

In addition to the foregoing, the recombinant vector of the invention may further contain, if desired, an enhancer, a splicing signal, a polyA addition signal, a ribosome binding sequence (SD sequence), a selection marker, etc., and provided for use. The selection marker includes, for example, a dihydrofolate reductase gene, an ampicillin resistance gene, a neomycin resistance gene, etc.

Preparation of Transformant

The thus obtained recombinant vector comprising the polynucleotide of the invention is introduced into an appropriate host to prepare the transformant. The host is not particularly limited as long as it is capable of expressing the polynucleotide (DNA) of the invention, and may be bacteria of the genera *Escherichia, Bacillus, Pseudomonas* and *Rhizobium*, yeast, animal cells or insect cells, etc. Bacteria of the genus *Escherichia* include *Escherichia coli*, etc. Bacteria of the genus *Bacillus* include *Bacillus subtilis*, etc. Bacteria of the genus *Pseudomonas* include *Pseudomonas putida*, etc. Bacteria of the genus *Rhizobium* include *Rhizobium meliloti*, etc. Yeast includes *Saccharomyces cerevisiae, Schizosaccharomyces pombe*, etc. Animal cells include primary cell cultures, iPS cells, cultured cell lines (CHO cells, HEK293 cells, HL-60 cells, HeLa cells, MDCK cells, NIH3T3 cells, PC12 cells), etc. Insect cells include Sf9, Sf21, etc.

The method of transfecting the recombinant vector into the host and the method of transformation by the same can be performed according to various general methods. The method for transfecting the recombinant vector into the host cell includes the calcium phosphate method (Virology, 52, 456-457 (1973)), the lipofection method (Proc. Natl. Acad. Sci. USA, 84, 7413 (1987)), the electroporation method (EMBO J., 1, 841-845 (1982)), etc. The method for transformation of the bacteria of the genus *Escherichia* includes the methods described in, e.g., Proc. Natl. Acad. Sci. USA, 69, 2110 (1972), Gene, 17, 107 (1982), etc. The method for transformation of the bacteria of the genus *Bacillus* includes the method described in Molecular & General Genetics, 168, 111 (1979), etc. The method for transforming yeast includes the method described in Proc. Natl. Acad. Sci. USA, 75, 1929 (1978), etc. The method for transformation of animal cells includes the method described in Virology, 52, 456 (1973), etc. The method for transformation of insect cells includes the method described in Bio/Technology, 6, 47-55 (1988), etc. Thus, the transformant transformed with the recombinant vector comprising the polynucleotide encoding the luciferase mutant of the invention (the polynucleotide of the invention) can be obtained.

Expression Vector and Transformant Comprising Low-Temperature Expression-Inducible Promoter Sequence An expression vector comprising the low-temperature expression-inducible promoter sequence is preferred as the expression vector among others.

Specifically, the expression vector comprising the low-temperature expression-inducible promoter sequence is intended to mean an expression vector comprising the following promoter sequence and coding sequence:

(1) a low-temperature expression-inducible promoter sequence; and, (2) a coding sequence comprising the polynucleotide of the invention.

The low-temperature expression-inducible promoter sequence is intended to mean a promoter sequence which is capable of inducing expression of the protein by lowering the temperature from the culture conditions under which host cells can grow. Examples of the low-temperature expression-inducible promoter are promoters for genes encoding cold shock proteins (cold shock genes). Examples of the cold shock gene promoters include those as described above.

The temperature at which the low-temperature expression-inducible promoter used in the invention is capable of inducing expression is generally 30° C. or less, preferably 25° C. or less, more preferably 20° C. or less, and most preferably 15° C. or less. In order to induce the expression more efficiently, however, the expression induction is generally performed at 5° C. or more, preferably at 10° C. or more, and most preferably at approximately 15° C.

In preparing the expression vector of the invention comprising the low-temperature expression-inducible promoter sequence, the pCold I vector, pCold II vector, pCold III vector and pCold IV vector (all manufactured by Takara Bio Inc.) can be suitably used as the vector for insertion of the polynucleotide of the invention. The protein can be produced as a soluble protein in the cytoplasm in a host cell when expression is performed in a prokaryotic host cell using these vectors.

Prokaryotic cells are preferred as the host into which the expression vector comprising the low-temperature expression-inducible promoter sequence is introduced, more preferably, *E. coli*, and particularly preferably, the BL21 and JM109 strains. Among others, the BL21 strain is most preferred. The BL21 and JM109 strains are available from, e.g., Novagen.

Temperatures for incubation at which the transformant carrying the expression vector comprising the low-temperature expression-inducible promoter sequence grows are generally 25 to 40° C. and preferably 30 to 37° C. Temperatures for inducing the expression are generally 4 to 25° C., preferably 10 to 20° C., more preferably 12 to 18° C., and most preferably 15° C.

4. Production of Luciferase Mutant of the Invention

The present invention further provides a method for producing the luciferase mutant of the invention, which comprises the steps of culturing the transformant described above to produce the luciferase mutant of the invention. The luciferase mutant of the invention can be produced, for example, by culturing the transformant described above under conditions where the polynucleotide (DNA) encoding the luciferase mutant of the invention can be expressed, producing/accumulating and then separating/purifying the luciferase mutant of the invention.

Incubation of Transformant

The transformant of the invention can be incubated in a conventional manner used for incubation of a host. By the incubation, the luciferase mutant of the invention is produced by the transformant and accumulated within the transformant or in the culture medium.

The medium used for culturing the transformant using bacteria of the genus *Escherichia* or the genus *Bacillus* as a host may be any of a natural medium and a synthetic medium as far as it is a medium which contains carbon sources, nitrogen sources, inorganic salts, etc. necessary for growth of the transformant, and in which the transformant can efficiently grow. Examples of carbon sources which can be used are carbohydrates such as glucose, fructose, sucrose, starch, etc.; organic acids such as acetic acid, propionic acid, etc.; alcohols such as ethanol, propanol, and the like. Examples of nitrogen sources which can be used include ammonia, ammonium salts of inorganic or organic acids such as ammonium chloride, ammonium sulfate, ammonium acetate, ammonium phosphate, etc., and other nitrogen-containing compounds, and further include peptone, meat extracts, corn steep liquor, and the like. Examples of inorganic salts include monobasic potassium phosphate, dibasic potassium phosphate, magnesium phosphate, magnesium sulfate, sodium chloride, ferrous sulfate, manganese sulfate, copper sulfate, calcium carbonate, etc. If necessary, antibiotics such as ampicillin or tetracycline can be added to the medium during incubation. Where the transformant transformed by the expression vector using an inducible promoter as the promoter is cultured, an inducer may also be added to the medium, if necessary. For example, when the transformant transformed by an expression vector using a Lac promoter is cultured, isopropyl-β-D-thiogalactopyranoside (IPTG), etc. may be added to the medium and indoleacrylic acid (IAA), etc. may be added to the medium in culturing the transformant transformed by an expression vector using a trp promoter.

When the host is bacteria of the genus *Escherichia*, incubation is performed generally at approximately 15 to 43° C. for approximately 3 to 24 hours. If necessary, aeration and agitation may be applied. When the host is bacteria of the genus *Bacillus*, incubation is performed generally at approximately 30 to 40° C. for approximately 6 to 24 hours. If necessary, aeration and agitation may be applied.

Media for incubation of the transformant when the host is yeast include Burkholder's minimal medium (Proc. Natl. Acad. Sci. USA, 77, 4505 (1980)) and an SD medium containing 0.5% (w/v) Casamino acids (Proc. Natl. Acad. Sci. USA, 81, 5330 (1984)). Preferably, the pH of the medium is adjusted to approximately 5 to 8. Incubation is performed generally at approximately 20 to 35° C. for approximately 24 to 72 hours. If necessary, aeration and agitation may be applied.

Media for culturing the transformant when the host is an animal cell include MEM medium supplemented with approximately 5 to 20% (v/v) fetal calf serum (Science, 122, 501 (1952)), DMEM medium (Virology, 8, 396 (1959)), etc. Preferably, the pH of the medium is adjusted to approximately 6 to 8. Incubation is performed generally at approximately 30 to 40° C. for approximately 15 to 60 hours. If necessary, aeration and agitation may be applied.

Media for culturing the transformant when the host is an insect cell include Grace's insect medium (Nature, 195, 788 (1962)) to which additives such as 10% (v/v) immobilized bovine serum are suitably added. Preferably, the pH of the medium is adjusted to approximately 6.2 to 6.4. Incubation is performed generally at approximately 27° C. for approximately 3 to 5 days. If necessary, aeration and agitation may be applied.

Temperatures for incubation at which the transformant transformed by the expression vector comprising the low-temperature expression-inducible promoter sequence and temperatures for expression induction are as described above.

Separation/Purification of Luciferase Mutant of the Invention

The luciferase mutant of the invention can be obtained by separating/purifying the luciferase mutant of the invention from the culture described above. As used herein, the culture is intended to mean any one of a culture broth, cultured cells or cultured bacteria and a cell lysate of the cultured cells or cultured bacteria. The luciferase mutant of the invention can be separated/purified in a conventional manner.

Specifically, when the luciferase mutant of the invention accumulates in the cultured bacteria or cultured cells, after completion of the incubation the bacteria or cells are disrupted in a conventional manner (e.g., ultrasonication, lysozyme, freezing and thawing, etc.,) and then a crude extract of the luciferase mutant of the invention can be obtained in a conventional manner (e.g., centrifugation, filtration, etc.). When the luciferase mutant of the invention accumulates in the periplasmic space, after completion of the incubation the extract containing the luciferase mutant of the invention can be obtained in a conventional manner (e.g., the osmotic shock method, etc.). When the luciferase mutant of the invention accumulates in the culture broth, after completion of the incubation the culture supernatant containing the luciferase mutant of the invention can be obtained by separating the bacteria or cells and the culture supernatant in a conventional manner (e.g., centrifugation, filtration, etc.).

The luciferase mutant of the invention contained in the extract or culture supernatant thus obtained can be purified by conventional methods of separation and purification. Examples of these methods for separation and purification which may be used include ammonium sulfate precipitation, gel filtration chromatography, ion-exchange chromatography, affinity chromatography, reversed-phase high-performance liquid chromatography, dialysis, ultrafiltration, etc., alone or in a suitable combination thereof. When the luciferase mutant of the invention contains the peptide sequence for purification described above, it is preferred to perform purification using the same. Specifically, when the luciferase mutant of the invention contains a histidine tag sequence, nickel chelate affinity chromatography may be used; when the luciferase mutant of the invention contains the binding domain of S-transferase to glutathione, affinity chromatography with a glutathione-binding gel may be used; when the luciferase mutant of the invention contains the amino acid sequence of Protein A, antibody affinity chromatography may be used.

5. Use of Luciferase Mutant of the Invention

Use as Detection Marker by Luminescence

The luciferase mutant of the invention can be used as a detection marker which emits luminescence in the presence of a luciferin (hereinafter "detection marker of the present invention"). The detection marker of the present invention can be utilized for detection of the target substance in, e.g., an immunoassay, a hybridization assay, etc.

The luciferase mutant of the invention can be expressed, e.g., as a fusion protein with a target protein, and introduced into cells by means of the microinjection method, etc., and the resulting product can be used to determine distribution of the target protein described above. The distribution of such a target protein or the like can be determined by using detection methods such as luminescence imaging. In addition to the introduction into cells by means of the microinjection method or the like, the luciferase mutant of the invention can be expressed in cells to provide for use.

The luminescence substrate (luciferin) used is preferably coelenterazines, and particularly preferably, bis-coelenterazine or 6h-f-coelenterazine, as described above. Bis-coelenterazine or 6h-f-coelenterazine displays the luminescence activity approximately 10 times higher than that of coelenterazine and emits glow.

Use as Reporter Protein

The luciferase mutant of the invention may also be used as a reporter protein to assay the transcription activity of promoters, etc. In this case, the polynucleotide of the invention is used as a reporter gene and the luciferase mutant encoded by the reporter gene is contacted with luciferin. As used herein, the term "contact" is intended to mean that the luciferase mutant of the invention and a luciferin are allowed to be present in the same reaction system or culture system, which includes, for example, addition of a luciferin to a culture container charged with cells expressing the luciferase mutant of the invention, mixing the cells with a luciferin, and incubation of the cells in the presence of a luciferin. The polynucleotide encoding the luciferase mutant of the invention (i.e., the polynucleotide of the invention) is fused to a target promoter or some other expression control sequence (e.g., an enhancer, etc.) to construct a vector. By introducing the vector into a host cell and detecting the luminescence from the luciferase mutant of the invention in the presence of a luciferin (luminescence substrate), the activity of the target promoter or some other expression control sequence can be assayed. Furthermore, the expressed luciferase mutant is reacted with coelenterazines and the luminescence generated may also be visualized in pictures by using a high-sensitive detector.

The luciferin used is preferably coelenterazines, and particularly preferably, bis-coelenterazine or 6h-f-coelenterazine, as described above, Bis-coelenterazine or 6h-f-coelenterazine displays the luminescence activity approximately 10 times higher than that of coelenterazine and emits glow.

The cells used are preferably animal cells. In the case of animal cells, the luciferase mutant in a preferred embodiment of the invention is secretion outside of cells.

The polynucleotide of the invention can be used as a reporter gene in such a manner as described above.

Method for Visualizing Luminescence Reaction

The luciferase mutant of the present invention can be used in the method for visualizing luminescence activities. By "visualizing luminescence activities," for example, the pattern of secretion can be observed when the luciferase mutant of the present invention is secreted extracellularly. The luciferase mutant of the invention is secreted extracellularly without passing through the trans-Golgi network, as will be demonstrated in EXAMPLES described below.

Specifically, the method for visualizing a luminescence reaction comprises contacting the luciferase mutant of the invention with a luciferin. As used herein, the term "contact" is intended to mean that the luciferase mutant of the invention and a luciferin are allowed to be present in the same reaction system or culture system, which includes, for example, addition of a luciferin to a culture container charged with cells expressing the luciferase mutant of the invention, mixing the cells with a luciferin and incubation of the cells in the presence of a luciferin. A vector comprising the polynucleotide encoding the luciferase mutant of the invention (i.e., the polynucleotide of the invention) is constructed. By introducing the vector into a host cell and detecting the luminescence from the luciferase mutant of the invention in the presence of a luciferin (luminescence substrate), the luminescence reaction can be visualized. In this case, the luminescence is detected by using, e.g., a high-sensitive detector.

The luciferin used is preferably coelenterazines, and particularly preferably, h-coelenterazine or f-coelenterazine, as described above. H-coelenterazine or f-coelenterazine displays the luminescence activity 10 times higher than that of coelenterazine and its light decays fast.

The cells used are preferably animal cells. Even in animal cells, the luciferase mutant in a preferred embodiment of the invention is secreted extracellularly.

The polynucleotide of the invention can be used in the method for visualizing a luminescence reaction in such a manner as described above.

Material for Amusement Supplies

The luciferase mutant of the invention has the activity of catalyzing the reaction where a luciferin is oxidized with oxygen molecules to for oxyluciferin its excited state. The oxyluciferin in the excited state emits visible light to decay to the ground state. Accordingly, the luciferase mutant of the invention can be used preferably as a luminescent material for amusement supplies. Examples of such amusement supplies are luminescent soap bubbles, luminescent ice bars, luminescent candies, luminescent color paints, etc. These amusement supplies of the invention can be prepared in a conventional manner.

The luciferin used is preferably coelenterazines, and particularly preferably, bis-coelenterazine or 6h-f-coelenterazine, as described above. Bis-coelenterazine or 6h-f-coelenterazine displays the luminescence activity approximately 10 times higher than that of coelenterazine and emits glow.

Bioluminescence Resonance Energy Transfer (BRET) Method

By utilizing the principle of interaction between molecules by the bioluminescence resonance energy transfer (BRET) method, the luciferase mutant of the invention is available for analytical methods such as analysis of physiological functions, assay of enzyme activities, etc.

For instance, when the luciferase mutant of the invention of the invention is used as a donor and the fluorescent substance (e.g., an organic compound, a fluorescent protein, etc.) is used as an acceptor, the interactions between the donor and acceptor above can be detected by inducing bioluminescence resonance energy transfer (BRET) between them.

In an embodiment of the present invention, the organic compound used as an acceptor includes Hoechist3342, Indo-1, DAP1, etc. In another embodiment of the present invention, the fluorescent protein used as an acceptor includes a green fluorescent protein (GFP), a blue fluorescent protein (BFP), a muted GFP fluorescent protein, phycobilin, etc. These organic compounds and fluorescent proteins are commercially available.

In a preferred embodiment of the present invention, the physiological functions to be analyzed include an orphan receptor (especially, a G protein-coupled receptor), apoptosis, transcription regulation by gene expression, etc. In a further preferred embodiment of the present invention, the enzyme to be analyzed is protease, esterase, kinase, or the like.

Analysis of the physiological functions by the BRET method can be performed by known methods, for example, by modifications of the method described in Biochem. J. 2005, 385, 625-637 or Expert Opin. Ther Tarets, 2007 11: 541-556. Enzyme activities may also be assayed by known methods, for example, by modifications of the method described in Nature Methods 2006, 3:165-174 or Biotechnol. J. 2008, 3:311-324.

The luminescence substrate (luciferin) used is preferably coelenterazines, and particularly preferably, bis-coelenterazine or 6h-f-coelenterazine, as described above. Bis-coelenterazine or 6h-f-coelenterazine displays the luminescence activity approximately 10 times higher than that of coelenterazine and emits glow.

6. Kit of the Invention

The present invention also provides a kit comprising any one selected from the luciferase mutant of the invention, the polynucleotide of the invention, the recombinant vector of the invention and the transformant of the invention. The kit of the invention may further contain a luciferin.

The luciferin is preferably coelenterazines, as described above. In some embodiments of the present invention, bis-coelenterazine or 6h-f-coelenterazine is particularly preferred. In some other embodiments of the present invention, h-coelenterazine or f-coelenterazine is particularly preferred in some embodiments of the present invention.

The kit of the present invention may be prepared with conventional materials by conventional methods. The kit of the present invention may further contain, e.g., sample tubes, plates, instructions for the kit user, solutions, buffers, reagents, and samples suitable for standardization or control samples. The kit of the present invention may further contain salts including halide ions.

The kit of the present invention can be used for the aforesaid measurement using a reporter protein or a reporter gene, the detection marker with luminescence, or the analysis of physiological functions or measurement of enzyme activities by the BRET method. The kit can also be used for the method for luminescence reaction as described below.

7. Method for Luminescence Reaction

Luminescence Activity

The luciferase mutant of the invention has the ability of catalyzing the reaction which involves oxidization of a luciferin with oxygen molecules to form an oxyluciferin in its excited state. The oxyluciferin in the excited state emits light on returning to the ground state. That is, the luciferase mutant of the invention catalyzes the luminescence reaction in which a luciferin serves as a substrate to cause luminescence. This activity is sometimes referred to as "the luminescence activity" in the specification.

Luminescence Reaction

The luminescence reaction using the luciferase mutant of the invention in which a luciferin serves as a substrate can be performed by contacting the luciferase mutant of the invention with the luciferin. As used herein, the term "contact" is intended to mean that the luciferase mutant of the invention and a luciferin are allowed to be present in the same reaction system, which includes, for example, addition of the luciferase mutant of the invention to a container charged with a luciferin, addition of a luciferin to a container charged with the luciferase mutant of the invention and mixing the luciferase mutant of the invention with a luciferin. The reaction can be carried out under conditions conventionally used for the luminescence reaction using *Oplophorus* luciferase or under conditions modified therefrom.

Specifically, solvents for the reaction which are employed are, for example, a buffer solution such as Tris-HCl buffer, sodium phosphate buffer, etc., water, and the like.

Temperatures for the reaction are generally approximately 4° C. to 40° C. and preferably approximately 4° C. to 25° C.

In the reaction solution, pH is generally approximately 5 to 10, preferably approximately 6 to 9, more preferably approximately 7 to 8 and most preferably approximately 7.5.

The luciferin is preferably coelenterazines, as described above. In some embodiments of the present invention, bis-coelenterazine or 6h-f-coelenterazine is particularly preferred. In some other embodiments of the present invention, h-coelenterazine or f-coelenterazine is particularly preferred.

The luciferin may also be added to the reaction system in the form of a solution in a polar solvent such as dimethylformamide, dimethylsulfoxide, etc., or in an alcohol such as methanol, ethanol, butanol, etc.

Activation of Luminescence Activity

The luminescence activity of the luciferase mutant of the invention can be activated by halide ions, nonionic surfactants, etc.

Examples of the halide ions are fluorine ions, chlorine ions, bromine ions and iodine ions; preferred are chlorine ions, bromine ions and iodine ions.

The concentration of halide ions is generally approximately 10 μM to 100 mM, preferably approximately 100 μM to 50 mM and particularly preferably approximately 1 mM to 20 mM.

The addition of the halide ions to the reaction system is performed by a method which comprises adding them in a salt form. The salts used are alkali metal salts such as sodium salts, potassium salts, etc.; alkaline earth metal salts such as calcium salts, magnesium salts, barium salts, etc. More specific examples are NaF, NaCl, NaBr, NaI, KF, KCl, KBr, KI, $CaF_2$, $CaCl_2$, $CaBr_2$, $CaI_2$, $MgF_2$, $MgCl_2$, $MgBr_2$, $MgI_2$, etc.

Examples of nonionic surfactants which are commercially available (trade name) include Tween 20 (polyoxyethylene sorbitan inonolaurate), Tween 80 (polyoxyethylene sorbitan monooleate), Triton X-100 (polyethylene glycol-p-isooctylphenyl ether), Briji-58 (polyoxyethylene (20) cetyl ether), Nonidet P-40 (ethyiphenolpoly(ethylene glycol ether)n), etc., and preferably, Tween 20, Triton X-100, etc. These surfactants are commercially available from, e.g., Wako Pure Chemical Industries, Ltd., Tokyo Chemical Industry Co., Ltd. and Sigma Aldrich.

Concentration of the nonionic surfactant is generally approximately 0.0002% (w/v) to 0.2% (w/v), preferably, approximately 0.001% (w/v) to 0.1% (w/v), and particularly preferably, approximately 0.05% (w/v) to 0.02% (w/v).

Regardless of their purposes, all of the documents and publications described in the specification are incorporated herein by reference, each in its respective entirety.

Unless otherwise indicated with respect to the embodiments and working examples, the methods described in standard sets of protocols such as J. Sambrook, E. F. Fritsch & T. Maniatis (Ed.), Molecular cloning, a laboratory manual (4th edition), Cold Spring Harbor Press, Cold Spring Harbor, N.Y. (2012); F. M. Ausubel, R. Brent, R. E. Kingston, D. D. Moore, J. G. Seidman, J. A. Smith, K. Struhl (Ed.), Current Protocols in Molecular Biology, John Wiley & Sons Ltd., etc. or modifications or variations thereof are used. When commercially available reagent kits or measuring apparatuses are used, protocols attached to them are used unless otherwise indicated.

The objects, characteristics and advantages of the present invention as well as the idea thereof are apparent to those skilled in the art from the descriptions given herein. Based on the description given herein, those skilled in the art can easily reproduce the present invention.

It can be understood that the embodiments of the invention, specific working examples, etc. are disclosed as preferred embodiments of the present invention. These descriptions are only for illustrative and explanatory purposes and are not intended to restrict the invention thereto. It is further apparent to those skilled in the art that various modifications may be made based on the descriptions given herein within the intent and scope of the present invention disclosed herein.

EXAMPLES

Hereinafter, the present invention will be described with reference to specific examples but is not deemed to be limited thereto.

Example 1

Preparation of Mutated 19kOLase Gene (dnKAZ) with 16 Mutations

Gene amplification was performed by PCR using a template of pCold-ZZ-P-nanoKAZ described in Inouye et al (2013) Biochem. Biophys. Res. Commun. 437: 23-28 and the following primers.
Primer nanoKAZ-1N/EcoRI (SEQ ID NO: 19: 5' gcg GAATTCTTCACCCTGGAGGACTTCGTCGGC 3': EcoRI sequence underlined)
Primer nanoKAZ-3C/XbaI (SEQ ID NO: 20: 5' gcc TCTAGATTAGGCCAGGATTCTCTCGCACAGTCT 3': XbaI sequence underlined)
Herein, the nucleotide sequence and amino acid sequence of pCold-ZZ-P-nanoKAZ are shown by SEQ ID NO: 11 and SEQ ID NO: 12, respectively. cl Example 2

Secretory Expression Vectors for dnKAZ Using the Secretory Signal Peptide Sequence of *Gaussia* Luciferase The expression vector for dnKAZ was constructed as follows. Firstly, a novel expression vector pcDNA3-GLsp in animal cultured cells was constructed. Specifically, the secretory signal peptide sequence of *Gaussia* luciferase was obtained from pcDNA3-GLuc vector (manufactured by Prolume Ltd.) by PCR using the following primers.
Primer GLsp-1R/EcoRI (SEQ ID NO: 21: 5' ggc GAATTCGGT GGG CTT GGC CTC GGC CAC 3', EcoRI sequence underlined)
T7 primer (SEQ ID NO: 22: 5' TAATACG ACTCACTATAGGG 3')

After digestion with HindIII/EcoRI, the resultant fragment was inserted into the HindIII-EcoRI site of pcDNA3 vector (manufactured by Invitrogen Inc.) to construct a novel expression vector pcDNA3-GLsp. That is, the novel expression vector is under the control of the CMV promoter, followed by the Kozak sequence, the secretory signal peptide sequence of *Gaussia* luciferase and a multiple-cloning site sequence.

Next, the expression vector for dnKAZ was constructed as follows, using the novel expression vector pcDNA3-GLsp. The DNA fragment obtained in EXAMPLE 1 was digested with the restriction enzymes of EcoRI/XbaI in a conventional manner and then ligated to the EcoRI-XbaI site of pcDNA3-GLsp to construct the expression vector pcDNA3-GLsp-dnKAZ. The gene sequence inserted was confirmed by sequencing using a DNA Sequencer (manufactured by ABI Inc.)

Example 3

Preparation of nanoKAZ Gene Fragments with the Deletion of Amino Acid Sequences at the Amino Terminal Region The gene fragments of nanoKAZ with the deletion of the amino acids at the amino terminal region were prepared in the following manner.

PCR (cycle conditions: 25 cycles of 1 min/94° C., 1 min/50° C. and 1 min/72° C.) was performed with a PCR kit (manufactured by Takara Bio Inc.) using pcDNA3-GLsp-dnKAZ obtained in EXAMPLE 2 as a temperate with two PCR primers.

In preparing, e.g., one amino acid-deleted ΔN2T-nKAZ mutant gene, PCR was performed using a pcDNA3-GLsp-dnKAZ as a template and the following two primers.
D2-nKAZ-15N/EcoRI (5'gccGAATTCAAGC TT GGTACCAC CATGGTCACCCTGGAGG ACTTCGTCGG CGAC 3': EcoRI sequence and KpnI sequence underlined) (SEQ ID NO: 23)
nanoKAZ-3C/XbaI (5'gccTCTAGA TTAGGCCAGG ATTCTCTCGC ACAGTCT 3') (SEQ ID NO: 20)

As a result, the gene (ΔN2T-nKAZ) encoding the amino acid sequence of nanoKAZ (SEQ ID NO: 2) with the deletion of the phenylalanine residue at the first amino acid was amplified. The nucleotide sequence of nanoKAZ gene is shown by SEQ ID NO: 1. The nucleotide sequence and amino acid sequence of ΔN2T-nKAZ are shown in SEQ ID NO: 3 and SEQ ID NO: 4, respectively.

The nanoKAZ genes deleted at the amino-terminal regions were obtained in a similar manner except for using the templates and primers described in TABLE 2. The amino-terminal sequences of the amino-terminal deleted nanoKAZ genes obtained are shown in TABLE 1.

Herein, the nucleotide sequence and amino acid sequence of ΔN3L-nKAZ are shown in SEQ ID NO: 5 and SEQ ID NO: 6, respectively. The nucleotide sequence and amino acid sequence of ΔN4E-nKAZ are shown in SEQ ID NO: 7 and SEQ ID NO: 8, respectively. The nucleotide sequence and amino acid sequence of ΔN5D-nKAZ are shown in SEQ ID NO: 9 and SEQ ID NO: 10, respectively.

TABLE 1

Amino acid sequence of amino-terminal deleted nanoKAZ gene

| Deletion mutant | Number of deleted amino acids | Amino-terminal sequence |
|---|---|---|
| nanoKAZ | 0 | FTLEDFVGDWRQTAGYNLDQVLEQG . . . |
| ΔN2T-nKAZ | 1 | TLEDFVGDWRQTAGYNLDQVLEQG . . . |
| ΔN3L-nKAZ | 2 | LEDFVGDWRQTAGYNLDQVLEQG . . . |
| ΔN4E-nKAZ | 3 | EDFVGDWRQTAGYNLDQVLEQG . . . |
| ΔN5D-nKAZ | 4 | DFVGDWRQTAGYNLDQVLEQG . . . |
| ΔN6F-nKAZ | 5 | FVGDWRQTAGYNLDQVLEQG . . . |
| ΔN7V-nKAZ | 6 | VGDWRQTAGYNLDQVLEQG . . . |
| ΔN8G-nKAZ | 7 | GDWRQTAGYNLDQVLEQG . . . |
| ΔN9D-nKAZ | 8 | DWRQTAGYNLDQVLEQG . . . |
| ΔN10W-nKAZ | 9 | WRQTAGYNLDQVLEQG . . . |
| ΔN15G-nKAZ | 14 | GYNLDQVLEQG . . . |
| ΔN20Q-nKAZ | 19 | QVLEQG . . . |

TABLE 2

Templates and PCR primers used for deletion of the amino-terminal sequence of nanoKAZ.

| Deletion mutant | Template | Primer | | Sequence |
|---|---|---|---|---|
| ΔN2T-nKAZ | pcDNA3-GLsp-dnKAZ | a | D2-nKAZ-15N/EcoRI | 5' gccGAATTCAAGC TTGGTACCAC CATGGTCACCCTGGAGG ACTTCGTCGG CAGC 3'(SEQ ID NO: 23) |
| | | b | nanoKAZ-3C/XbaI | 5' gccTCTAGA TTAGGCCAGG ATTCTCTCGC ACAGTCT 3'(SEQ ID NO: 20) |
| ΔN3L-nKAZ | pcDNA3-GLsp-dnKAZ | a | D3-nKAZ-16N/ECoRI | 5' gccGAATTCAAGC TTGGTACCAC CATGGTCCTGGAGG ACTTCGTCGG CGACTGG 3'(SEQ ID NO: 24) |
| | | b | nanoKAZ-3C/XbaI | 5' gccTCTAGA TTAGGCCAGG ATTCTCTCGC ACAGTCT 3'(SEQ ID NO: 20) |
| ΔN4E-nKAZ | pcDNA3-GLsp-dnKAZ | a | D4-nKAZ-17N/ECoRI | 5' gccGATTCAAGC TTGGTACCAC CATGGTCGAGG ACTTCGTCGG CGACTGGAGA 3'(SEQ ID NO: 25) |
| | | b | nanoKAZ-3C/XbaI | 5' gccTCTAGA TTAGGCCAGG ATTCTCTCGC ACAGTCT 3'(SEQ ID NO: 20) |
| ΔN5D-nKAZ | pcDNA3-GLsp-dnKAZ | a | D5nanoKAZ-4N/EcoRI | 5' gccGAATTCAAGC TTGGTACCAC CATGGTCG ACTTCGTCGG CGACTGGAGACAGA 3'(SEQ ID NO: 26) |
| | | b | nanoKAZ-3C/XbaI | 5' gccTCTAGA TTAGGCCAGG ATTCTCTCGC ACAGTCT 3'(SEQ ID NO: 20) |
| ΔN6F-nKAZ | pcDNA3-GLsp-dnKAZ | a | D6nanoKAZ-8N EcoRI | 5' gccGAATTCAAGC TTGGTACCAC CATGGTC TTCGTCGG CGACTGGAGACAGACC 3'(SEQ ID NO: 27) |
| | | b | nanoKAZ-3C/XbaI | 5' gccTCTAGA TTAGGCCAGG ATTCTCTCGC ACAGTCT 3'(SEQ ID NO: 20) |
| ΔN7V-nKAZ | pcDNA3-GLsp-dnKAZ | a | D7nanoKAZ-9N/EcoRI | 5' gccGAATTCAAGC TTGGTACCAC CATGGTCGTCGG CGACTGGAGACAGACCGCC 3'(SEQ ID NO: 28) |
| | | b | nanoKAZ-3C/XbaI | 5' gccTCTAGA TTAGGCCAGG ATTCTCTCGC ACAGTCT 3'(SEQ ID NO: 20) |
| ΔN8G-nKAZ | pcDNA3-GLsp-dnKAZ | a | D8nanoKAZ-10N/EcoRI | 5' gccGAATTCAAGC TTGGTACCAC CATGGTCGG CGACTGGAGACAGACCGCCG GC 3'(SEQ ID NO: 29) |
| | | b | nanoKAZ-3C/XbaI | 5' gccTCTAGA TTAGGCCAGG ATTCTCTCGC ACAGTCT 3'(SEQ ID NO: 20) |
| ΔN9D-nKAZ | pcDNA3-GLsp-dnKAZ | a | D9nanoKAZ-11N/EcoRI | 5' gccGAATTCAAGC TTGGTACCAC CATGGTCGACTGGAGACAGACCGCCG GCTAC 3'(SEQ ID NO: 30) |
| | | b | nanoKAZ-3C/XbaI | 5' gccTCTAGA TTAGGCCAGG ATTCTCTCGC ACAGTCT 3'(SEQ ID NO: 20) |
| ΔN10W-nKAZ | pcDNA3-GLsp-dnKAZ | a | D10nanoKAZ-5N/EcoRI | 5' gccGAATTCAAGC TTGGTACCAC CATGGTCTGGAGACAGACCGCCG GCTACAACC 3'(SEQ ID NO: 31) |
| | | b | nanoKAZ-3C/XbaI | 5' gccTCTAGA TTAGGCCAGG ATTCTCTCGC ACAGTCT 3'(SEQ ID NO: 20) |
| ΔN15G-nKAZ | pcDNA3-GLsp-dnKAZ | a | D15nanoKAZ-6N/EcoRI | 5' gccGAATTCAAGC TTGGTACCAC CATGGTCG GCTACAACCT GGACCAGGTC CTGG 3'(SEQ ID NO: 32) |
| | | b | nanoKAZ-3C/XbaI | 5' gccTCTAGA TTAGGCCAGG ATTCTCTCGC ACAGTCT 3'(SEQ ID NO: 20) |
| ΔN20Q-nKAZ | pcDNA3-GLsp-dnKAZ | a | D20nanoKAZ-7N/EcoRI | 5' GCCGAATTCAAGC TTGGTACCAC CATGGTCCAGGTC CTGGAGCAGG GCGGCGTCA 3'(SEQ ID NO: 33) |
| | | b | nanoKAZ-3C/XbaI | 5' gccTCTAGA TTAGGCCAGG ATTCTCTCGC ACAGTCT 3'(SEQ ID NO: 20) |

Example 4

Construction of E. coli Expression Vectors for Amino-Terminal Deleted nanoKAZ Using a pColdII Vector The DNA fragment obtained in EXAMPLE 3 was purified with a PCR purification kit (manufactured by QIAGEN Inc.), digested with the restriction enzymes of EcoRI and XbaI and then ligated to the EcoRI-XbaI site in the expression vector of pColdII (Takara Bio Inc.) to construct the expression vectors, pCold-ΔN5D-nKAZ, pCold-ΔN6F-nKAZ, pCold-ΔN7V-nKAZ, pCold-ΔN8G-nKAZ, pCold-ΔN9D-nKAZ and pCold-ΔN10W-nKAZ for the amino-terminal deleted nanoKAZ.

Also, the pCold-ZZ-P-nanoKAZ described in EXAMPLE 1 was digested with the restriction enzymes of EcoRI and XbaI in a conventional manner and then ligated to the EcoRI-XbaI site in the expression vector of pColdII to construct the pCold-nanoKAZ vector. The nucleotide sequence of the inserted DNA was confirmed by sequencing using a DNA Sequencer (manufactured by ABI Inc.). The nucleotide sequence and amino acid sequence of pCold-nanoKAZ are shown in SEQ ID NO: 13 and SEQ ID NO: 14, respectively.

Example 5

Expression of Amino-Terminal Deleted nanoKAZ in E. coli and Preparation of Crude Enzyme Solution In order to express the amino-terminal deleted nanoKAZ in *E. coli*, the recombinant plasmid obtained in EXAMPLE 4 was used. The *E. coli* BL21 strain (Novagen, Madison, Wis.) was used as a host cell. The BL21 strain carrying the recombinant plasmid was incubated in 5 mL of Luria-Bertani medium (hereinafter designated as LB medium) containing ampicillin (50 ↑g/mL) at 37° C. for 18 hours. The seed culture of 0.1 mL was inoculated to 10 mL of LB medium and incubated for 3 hours, followed by cooling in an ice-water bath for 1 hour. IPTG was added to the culture medium at a final concentration of 0.1 mM, followed by incubation at 15° C. for further 17 hours. After completion of the incubation, 1 mL of the culture medium was collected by centrifugation at 10,000 rpm for 2 minutes. The collected *E. coli* cells were suspended in 0.5 mL of 30 mM Tris-HCl (pH 7.6)-10 mM EDTA (manufactured by Wako Pure Chemical Industries, Ltd.) (hereinafter designated as TE). The *E. coli* cells were disrupted by sonication for 3 seconds using a Branson model 250 sonifire (Danbury, Conn.) to give a crude enzyme solution. Then, 5 μL of the crude enzyme solution was analyzed by SDS-PAGE to confirm the protein expression (FIG. 1).

In FIG. 1, labeled M and 1 to 7 represnt as follows: M: molecular weight size markers; 1: nanoKAZ, 2: ΔN5D-nKAZ, 3: ΔN6F-nKAZ, 4: ΔN7V-nKAZ, 5: ΔN8G-nKAZ, 6: ΔN9D-nKAZ and 7: ΔN10W-nKAZ.

Example 6

Construction of E. coli Expression Vectors for ZZ-Fused Amino-Terminal Deleted nanoKAZ To express the amino-terminal deleted nanoKAZ as a soluble protein, the expression vector of pCold-ZZ-X (described in Inouye & Sahara, Protein Express. Purif. (2009) 66: 52-57) was used. The DNA fragment obtained in EXAMPLE 3 was digested with the restriction enzyme of EcoRI and XbaI and ligated to the EcoRI-XbaI site of pCold-ZZ-X to construct the following 11 expression vectors for the ZZ-fused amino-terminal deleted nanoKAZ: pCold-ZZ-P-ΔN2T-nKAZ, pCold-ZZ-P-ΔN3L-nKAZ, pCold-ZZ-P-ΔN4E-nKAZ, pCold-ZZ-P-ΔN5D-nKAZ, pCold-ZZ-P-ΔN6F-nKAZ, pCold-ZZ-P-ΔN7V-nKAZ, pCold-ZZ-P-ΔN8G-nKAZ, pCold-ZZ-P-ΔN9D-nKAZ, pCold-ZZ-P-ΔN10W-nKAZ, pCold-ZZ-P-ΔN15G-nKAZ and pCold-ZZ-P-ΔN20Q-nKAZ.

Example 7

Expression of ZZ-Fused Amino-Terminal Deleted nanoKAZ in E. coli and Preparation of Crude Enzyme Solution To express the ZZ-fused amino-terminal deleted nanoKAZ in *E. coli*, the recombinant plasmid obtained in EXAMPLE 6 was used. Crude enzyme solutions were prepared using a similar manner to EXAMPLE 5 using the *E. coli* BL21 strain (Novagen, Madison, Wis.) as a host cell. Then, 5 μL of the crude enzyme solution obtained was subjected to SDS-PAGE analysis to confirm the protein expression (FIG. 2).

Figure 2:
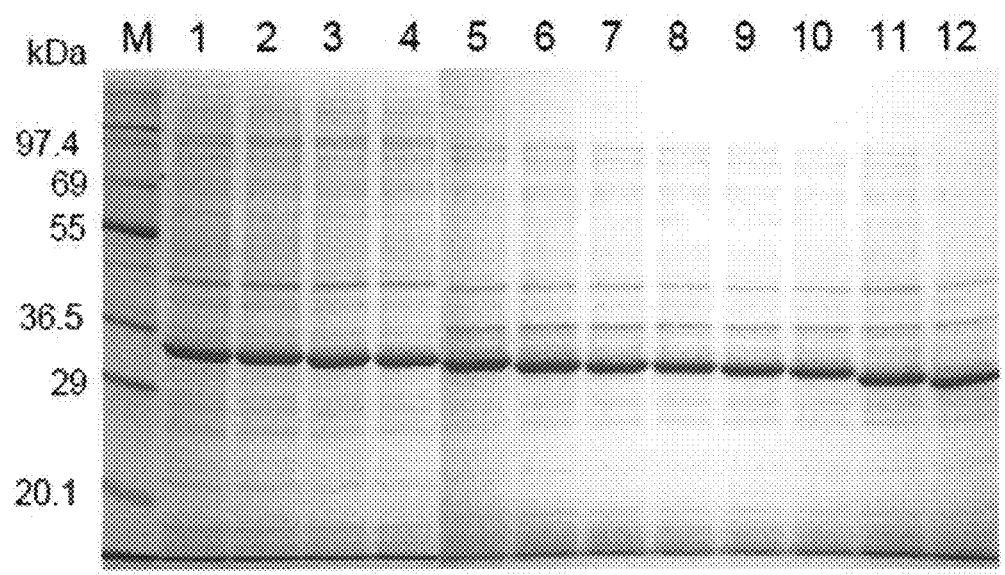
FIG. 2 shows the results of SDS-PAGE analysis of the crude enzyme solution of *E. coli* in which the amino-terminal deleted nanoKAZ was expressed using a pCold-ZZ-P vector.

In FIG. 2, labeled M and 1 to 12 represnt as follows. M: molecular weight size markers; 1: ZZ-P-nanoKAZ, 2: ZZ-P-ΔN2T-nKAZ, 3: ZZ-P-ΔN3L-nKAZ, 4: ZZ-P-ΔN4E-nKAZ, 5: ZZ-P-ΔN5D-nKAZ, 6: ZZ-P-ΔN6F-nKAZ, 7: ZZ-P-ΔN7V-nKAZ, 8: ZZ-P-ΔN8G-nKAZ, 9: ZZ-P-ΔN9D-nKAZ, 10: ZZ-P-ΔN10G-nKAZ, 11: ZZ-P-ΔN15G-nKAZ and 12: ZZ-P-ΔN20Q-nKAZ.

Example 8

Assay for Luminescence Activity of Amino-Terminal Deleted nanoKAZ and ZZ-Fused Amino-Terminal Deleted nanoKAZ in Crude Enzyme Solution The crude enzyme solutions obtained in EXAMPLE 5 and EXAMPLE 7 were allowed to stand in an ice-water for over 1 hour and then diluted to 50-fold in TE. By addition of 1 μL each of the crude enzyme solutions to 100 μL of TE containing 1 μg of coelenterazine (manufactured by JNC Corp.), a luminescence reaction was started. The luminescence activity was measured for 60 seconds using a luminometer (manufactured by Atto Inc.: AB2200); the maximum intensity of luminescence ($I_{max}$) is given as a percentage (%).

The luminescence activities of nanoKAZ, when expressed in *E. coli*, were markedly reduced by deletion of 8 or more amino acid residues at the amino-termius of nanoKAZ. As the deletions up to 5 amino acid resdues at the amino-terminnus showed 40 to 60% luminescence activity, it was clear that the amino-terminal region of nanoKAZ had no direct effects on the luminescence activity.

TABLE 3

Luminescence activity of amino-terminal deleted nanoKAZ in crude enzyme solution

| Deletion mutant | Relative luminescence activity (%, $I_{max}$) | |
|---|---|---|
| | pCold- | pCold-ZZ-P- |
| nanoKAZ | 100 | 100 |
| ΔN2T-nKAZ | — | 93.4 |
| ΔN3L-nKAZ | — | 82.0 |
| ΔN4E-nKAZ | — | 74.0 |
| ΔN5D-nKAZ | 87.0 | 73.6 |
| ΔN6F-nKAZ | 40.0 | 59.8 |
| ΔN7V-nKAZ | 1.6 | 5.8 |
| ΔN8G-nKAZ | 3.9 | 10 |
| ΔN9D-nKAZ | 0.01 | 0.3 |
| ΔN10W-nKAZ | 0.03 | 1.6 |
| ΔN15G-nKAZ | — | 0 |
| ΔN20Q-nKAZ | — | 0 |

Example 9

Secretory Expression Vectors for Amino-Terminal Deleted nanoKAZ Mutants Using a Secretory Signal Peptide Sequence of Gaussia Luciferase From the results of expression of the amino-terminal deleted nanoKAZ in *E. coli*, detectable luminescence activities were observed in the mutants with deletions up to 9 amino acid residues from the amino terminus (ΔN10W-nKAZ). In order to confirm that these deletion mutants could be secreted from animal cultured cells, the expression vectors for the amino-terminal deleted nanoKAZ in animal cultured cells were constructed.

Specifically, the amino-terminal deleted nanoKAZ gene fragment obtained in EXAMPLE 3 was digested with the restriction enzymes of EcoRI and XbaI in a conventional manner and then ligated to the EcoRI-XbaI site of pcDNA3-GLsp obtinaed in EXAMPLE 2 to construct the expression vectors as follows; pcDNA3-GLsp-ΔN2T-nKAZ, pcDNA3-GLsp-ΔN3L-nKAZ, pcDNA3-GLsp-ΔN4E-nKAZ, pcDNA3-GLsp-ΔN5D-nKAZ, pcDNA3-GLsp-ΔN6F-nKAZ, pcDNA3-GLsp-ΔN7V-nKAZ, pcDNA3-GLsp-ΔN8G-nKAZ, pcDNA3-GLsp-ΔN9D-nKAZ, pcDNA3-GLsp-ΔN10W-nKAZ and pcDNA3-GLsp-ΔN15G-nKAZ and pcDNA3-GLsp-ΔN20Q-nKAZ.

Also, the pCold-ZZ-P-nanoKAZ vector obtained in EXAMPLE 1 was digested with the restriction enzymes of EcoRI and XbaI in a conventional manner and then ligated to the EcoRI-XbaI site in the expression vector of pcDNA3-GLsp to construct the pcDNA3-GLsp-nanoKAZ vector.

The gene sequences inserted were confirmed by sequencing using a DNA sequencer (manufactured by ABI Inc.). The nucleotide sequence and amino acid sequence of pcDNA3-GLsp-nanoKAZ are shown in SEQ ID NO: 15 and SEQ ID NO: 16, respectively.

Example 10

Transfection of Vectors in Animal Culture Cells and Preparation of Enzyme for Assay (1) Purification of Expression Plasmid The following experiment was performed using the recombinant plasmids obtained in EXAMPLE 9. The recombinant plasmid was purified from *E. coli* JM83 strain using a plasmid purification kit (manufactured by QIAGEN) and dissolved in sterilized water. The firefly luciferase vector (pGL4.13 [Luc2/sv40]: manufactured by Promega Corp.) was similarly prepared and used as an internal standard.

(2) Transfection and Preparation of Enzyme for Assay

Chinese hamster ovary cell line CHO-K1 was cultured in Ham's F-12 medium (manufactured by Wako Pure Chemical Industries, Ltd.) supplemented with 10% (v/v) fetal bovine serum (manufactured by Biowest Inc.) (hereinafter sometimes referred to as Ham's F-12 medium). The CHO-K1 cells were seeded in a 6-well plate in $1 \times 10^5$ cells/well/2 mL medium (n=2) and cultured in an incubator at 37° C. in 5% (v/v) $CO_2$. After 24 hours, the purified recombinant plasmid was transfected to CHO-K1 cells using a FuGene HD transfection kit (manufactured by Promega Corp.) and the cells were provided for subsequent experiment. Specifically, 1 μg of the recombinant plasmid, 0.1 μg of the internal standard vector pGL4.13 [Luc2/sv40] and 3 μL of FuGene HD were added to 100 μL of the medium and allowed to stand at room temperature for 15 minutes. Subsequently, 100 μL of the DNA-FuGene complex was added to the cells in the 6-well plate. After incubation for 44 hours, the culture medium was collected. On the other hand, the cells expressed the KAZ mutants were washed 3 times with 3 mL of 1× PBS, then suspended in 1 mL of 1× PBS and disrupted by sonication on ice. The resultant cell extracts of nanoKAZ deletion mutants was used as enzyme solutions.

Example 11

Construction of Vectors for the Amino-Terminal Deleted nanoKAZ Lacking the Secretory Signal Peptide Sequence in Animal Cultured Cells After digestion of the gene fragment of amino-terminal deleted nanoKAZ obtained in EXAMPLE 3 with the restriction enzymes of Asp718 and XbaI, the fragment was inserted into the Asp718-XbaI site of a pcDNA3 vector (manufactured by Invitrogen Inc.) to construct the vectors, pcDNA3-ΔN2T-nKAZ, pcDNA3-ΔN3L-nKAZ, pcDNA3-ΔN4E-nKAZ, pcDNA3-ΔN5D-nKAZ, pcDNA3-ΔN6F-nKAZ, pcDNA3-ΔN7V-nKAZ, pcDNA3-ΔN8G-nKAZ, pcDNA3-ΔN9D-nKAZ, pcDNA3-ΔN10W-nKAZ, pcDNA3-ΔN15G-nKAZ and pcDNA3-ΔN20Q-nKAZ.

Also, the pCold-ZZ-P-nanoKAZ obtained in EXAMPLE 1 was digested with the restriction enzymes of Asp718/XbaI in a conventional manner and then similarly ligated to the Asp718-XbaI site of a pcDNA3 vector to construct the pcDNA3-nanoKAZ vector. The nucleotide sequence and amino acid sequence of nanoKAZ in pcDNA3-nanoKAZ are shown in SEQ TD NO: 17 and SEQ ID NO: 18, respectively.

Example 12

Transfection of Vectors in Animal Cultured Cells and Preparation of Enzyme for Assay (1) Purification of Expression Plasmids The recombinant plasmids obtained in EXAMPLE 11 were purified in a similar manner to EXAMPLE 10 and dissolved in sterilized water. The firefly luciferase vector (pGL4.13 [Luc2/sv40]: manufactured by Promega Corp.) was similarly prepared and used as an internal standard.

(2) Transfection and Preparation of Enzyme for Assay

Culture media containing the secreted amino-terminal deleted nanoKAZ and cell extracts of amino-terminal deleted nanoKAZ as the enzyme solutions were prepared in the same manner as in EXAMPLE 10.

Example 13

Assay for Luminescence Activity of Amino-Terminal Deleted nanoKAZ Expressed in Animal Cultured Cells After adding of 5 μL each of the culture media and cell extracts obtained in EXAMPLE 10 and EXAMPLE 12, respectively, to 100 μL of TE containing 1 μg of coelenterazine (manufactured by JNC Corp.), a luminescence reaction was started. The luminescence activity was measured for 60 seconds using a luminometer (manufactured by Atto Inc.: AB2200), and the maximum intensity of luminescence ($I_{max}$) was given as a percentage (%).

As a result, luminescence activities of the amino-terminal deleted nanoKAZ mutants with the secretory signal peptide sequence of *Gaussia* luciferase were observed in the cytoplasm of ΔN2T-nKAZ to ΔN8G-nKAZ and in the culture media of ΔN2T-nKAZ to ΔN6F-nKAZ.

On the other hand, in the amino-terminal deleted nanoKAZ lacking the secretory signal peptide sequence, the mutants including those up to ΔN5-nKAZ with 4 amino acids deletion from the amino terminus were found to be secreted into the culture medium, but no secretion from the cells was observed in the nanoKAZ mutants with the deletion of 5 or more amino acid residues from the amino terminus. Thus, it became clear that the nanoKAZ mutants with the deletion of at least one to at most 4 amino acids at the amino terminal region could be secreted extracellularly in the absence of the secretory signal peptide sequence.

Regarding firefly luciferase used as an internal standard to confirm the efficiency of transfection, 5 μL each of cell extracts obtained in EXAMPLES 10 and 12 were added to 100 μL of a reagent for enzyme assay (manufactured by Promega Corp.) to start a luminescence reaction. The luminescence activity was measured for 10 seconds using a luminometer (manufactured by Atto Inc.: AB2200). The results reveal that the transfection efficiencies were almost the same.

TABLE 4

Luminescence activities of amino-terminal deleted nanoKAZ in culture medium and cell extracts

| Deletion mutant | Relative luminescence activity (%, $I_{max}$) | | | |
|---|---|---|---|---|
| | pcDNA3-GLsp- | | pcDNA3- | |
| | Culture medium | Cell extracts | Culture medium | Cell extracts |
| nanoKAZ | 100 | 4.8 | 100 | 29.4 |
| ΔN2T-nKAZ | 97.0 | 3.4 | 93.4 | 23.3 |
| ΔN3L-nKAZ | 87.7 | 4.4 | 50.6 | 16.2 |
| ΔN4E-nKAZ | 60.5 | 2.9 | 4.6 | 9.7 |
| ΔN5D-nKAZ | 56.2 | 1.7 | 0.1 | 1.5 |
| ΔN6F-nKAZ | 0.5 | 0.3 | less than 0.01 | 0.06 |
| ΔN7V-nKAZ | 0 | 0.1 | 0 | less than 0.01 |
| ΔN8G-nKAZ | 0 | 0.2 | 0 | 0.01 |
| ΔN9D-nKAZ | 0 | 0 | 0 | 0 |
| ΔN10W-nKAZ | 0 | 0 | 0 | 0 |
| ΔN15G-nKAZ | 0 | 0 | 0 | 0 |
| ΔN20Q-nKAZ | 0 | 0 | 0 | 0 |

From the confirmed results of the activity for the KAZ mutants expressed in *E. coil* in EXAMPLE 8 and of the secretion from animal cultured cells in EXAMPLE 13, the nanoKAZ mutants with 1, 2, 3 and 4 amino acid residues deletion from the amino terminus were secreted into the culture medium from the animal cultured cells The results reveal that the sequence(s) of at least one to at most 4 amino acid residues from the amino terminus are related to the extracellular secretion of nanoKAZ.

Example 14

Preparation of CHO-K1 Cell Line Stably Expressing nanoKAZ Having the Secretory Signal Peptide Sequence of *Gaussia* Luciferase Chinese hamster ovary cell line CHO-K1 was cultured in Ham's F-12 medium. The CHO-K1 cells were seeded in a 6 cm petri dish in $2 \times 10^5$ cells/well/2 mL medium (n=2) and cultured in an incubator at 37° C. in 5% (v/v) $CO_2$. After 24 hours, the purified pcDNA3-GLsp-nanoKAZ described in EXAMPLE 10 was transfected to CHO-K1 cells using a FuGene HD transfection kit (manufactured by Promega Corp.).

The CHO-K1 cells transfected were treated with trypsin and were resuspended in 5 mL of Ham's F-12 medium. The cell suspension of $0.5 \times 10^5$ cells were plated in six petri dishes of 10 cm with 10 mL of Ham's F-12 medium. After overnight incubation at 37° C. in a 5% $CO_2$ incubator, 160 μL (a final concentration of 800 μL/mL) of 50 mg/mL G418 sulfate (manufactured by Calbiochem, Inc.) was added thereto, followed by incubation at 37° C. in a 5% $CO_2$ incubator for 7 days.

Seven days later, 48 colonies formed were picked with a sterilized toothpick and suspended in 50 μL of trypsin solution in a 96-well plate. To 50 μL each of the 48 trypsinized-cell suspensions was added 100 μL of Ham's F-12 medium. Each mixture was added to a 24-well plate with 1 mL of Ham's F-12 medium containing G418. The cells were incubated at 37° C. in a 5% $CO_2$ incubator for about 7 days until the cells grew.

After the cells grew, 5 μL of the culture medium was recovered and added to 100 μL of TE containing 0.5 μg of coelenterazine, and the luminescence activity was determined. The cell lines showing a high luminescence activity were treated with trypsin and suspended in 1 mL of Ham's F-12 medium containing G418. After 50 μL of the cell suspension was added to a 24-well plate with 1 mL of Ham's F-12 medium containing G418, the cells were incubated at 37° C. in a 5% $CO_2$ incubator for about 5 days until the cells grew.

After the cells grew, the luminescence activity was determined in a similar manner. The cell lines showing a high luminescence activity were treated with trypsin and suspended in 1 mL of Ham's F-12 medium containing G418. After 200 μL of the cell suspension was added to a 6-well plate with 3 mL of Ham's F-12 medium containing G418, the cells were incubated at 37° C. in a 5% $CO_2$ incubator for about 5 days until the cells grew.

After the cells grew, the luminescence activity was determined in a similar manner. The cell lines showing a high luminescence activity were treated with trypsin and suspended in 1 mL of Ham's F-12 medium containing G418 After 500 μL of the cell suspension was added to a 10 cm petri dish with 10 mL of Ham's F-12 medium containing G418, the cells were incubated at 37° C. in a 5% $CO_2$ incubator for approximately 3 to 5 days until the cells grew.

After the cells grew, the luminescence activity was determined in a similar manner to confirm that the cells showed a high luminescence activity. The CHO-K1 cell line stably expressing nanoKAZ having a secretory signal peptide sequence of *Gaussia* luciferase was obtained.

Example 15

Preparation of CHO-K1 Stably Expressing nanoKAZ Lacking the Secretory Signal Peptide Sequence The CHO-K1 cell line stably expressing nanoKAZ in the absence of the secretory signal peptide sequence was obtained in a similar manner to EXAMPLE 14, except that pcDNA3-nanoKAZ purified in EXAMPLE 13 as a plasmid DNA for transfection was used.

Example 16

Comparison of Secretory Inhibition by Brefeldin A

Using the stable expressed cell lines established in EXAMPLE 14 and EXAMPLE 15, the effect of brefeldin A that inhibits exocytosis through the trans-Golgi network by the vesicle-mediated transport was compared. Specifically, each stable expressed cell lines with $2 \times 10^5$ cells were seeded to a 6-well plate in 3 mL of Ham's F-12 medium containing 10% FBS, respectively, followed by incubation at 37° C. in a 5% $CO_2$ incubator for 48 hours. After washing twice with 3 mL Ham's F-12 medium containing 10% FBS, brefeldin A (manufactured by Wako Pure Chemical Industries, Ltd.) was added to the culture medium at a final concentration of 5 µg/mL. As a control experiment, cells were cultured in the absence of brefeldin A. The luminescence activity in the culture medium was determined at each incubation times at 0, 1, 3 and 6 hours, using coelenterazine as a substrate. The results are shown in FIGS. 3 and 4.

Figure 3:
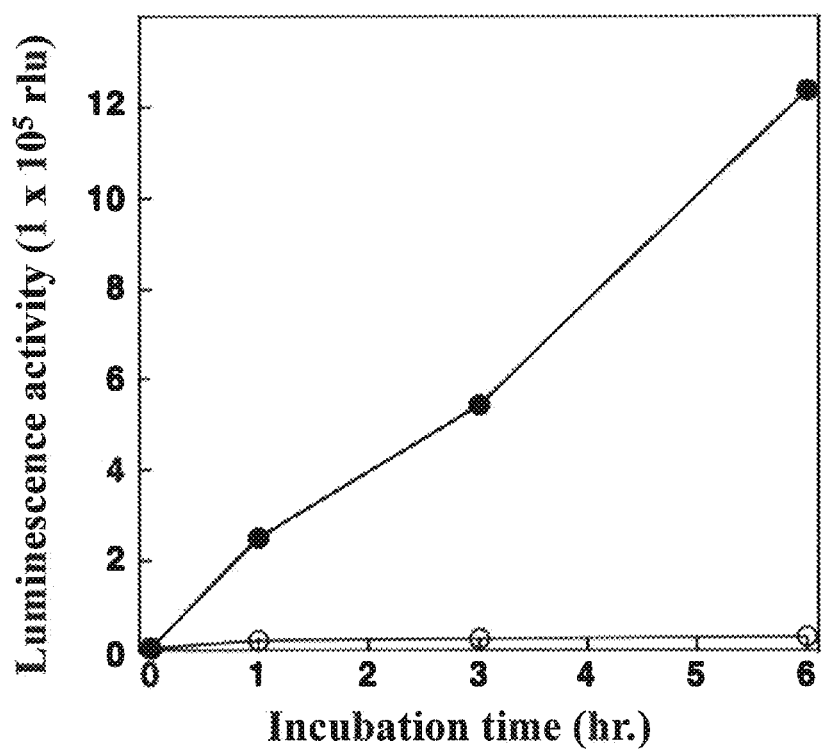
FIG. 3 shows the secretory inhibition of nanoKAZ by brefeldin A from the stable expressed cell line, pcDNA3-GLsp-nanoKAZ/CHO-K1, which was established using the nanoKAZ gene with a secretory signal peptide sequence. Open circles and closed circles indicate the presence and absence of brefeldin A, respectively.

As shown in FIG. 3, the secretion of nanoKAZ into the culture medium was markedly inhibited by brefeldin A in the pcDNA3-GLsp-nanoKAZ/CHO-K1 stable expressed cell line established using the nanoKAZ gene with the secretory signal peptide sequence, as compared to the cells in the absence of brefeldin A. This indicates that nanoKAZ having the secretory signal peptide sequence was secreted normally from a endoplasmic reticulum via the trans-Golgi network.

Figure 4:
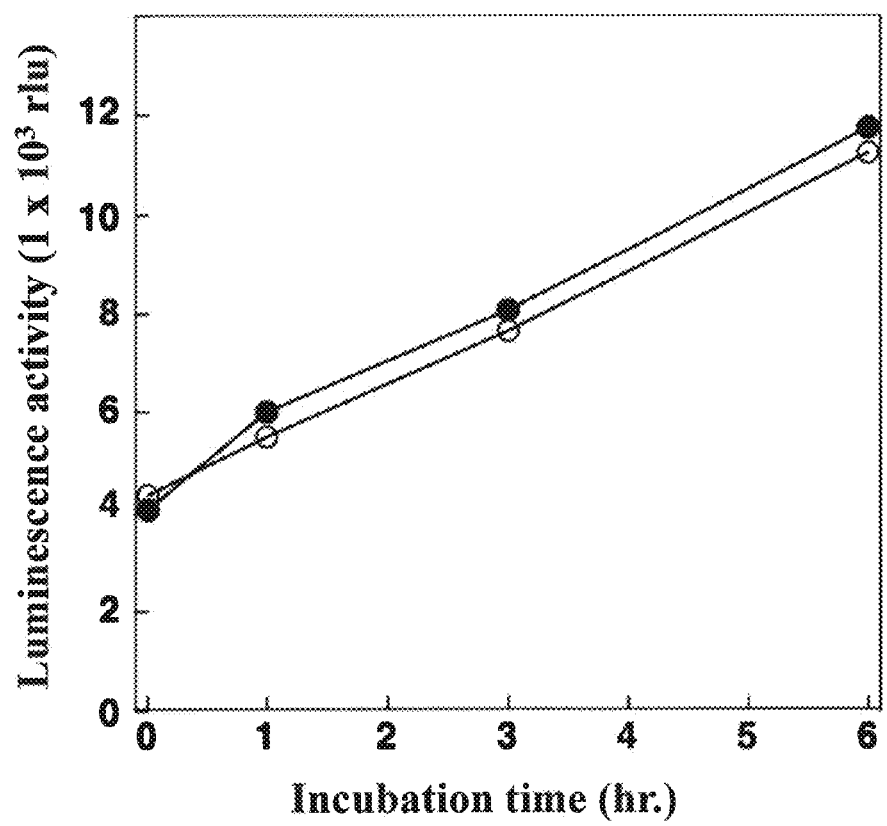
FIG. 4 shows the secretion of nanoKAZ from the stable expressed cell line, pcDNA3-nanoKAZ/CHO-K1, which was established using the nanoKAZ gene lacking a secretory signal peptide sequence, in the presence of brefeldin A. Open circles and closed circles indicate the presence and absence of brefeldin A, respectively.

On the other hand, as shown in FIG. 4, the nanoKAZ was secreted from the pcDNA3-nanoKAZ/CHO-K1 stable expressed cell line established using the nanoKAZ gene without the secretory signal peptide sequence in the presence or absence of brefeldin A. This indicates that the protein was secreted through another pathway(s), not through a general trans-Golgi network from the endoplasmic reticulum.

From the foregoing results and the results of the experiments on the amino-terminal deleted nanoKAZ gene expression described in EXAMPLES 8 and 13, it was demonstrated that the amino-terminal region at the positions of 1 to 4 from the amino terminus of nanoKAZ, has different secretion information from a general signal peptide sequence for secretion.

Example 17

Visualization of nanoKAZ Secretion

Figure 5:
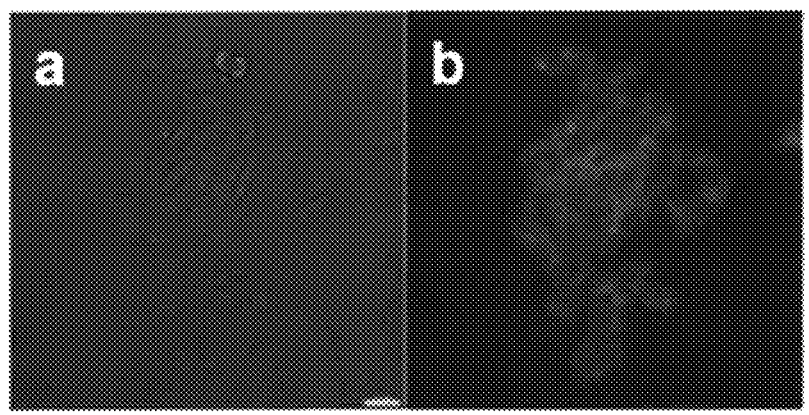
FIG. 5 shows the bright-field image and the visualized luminescence image of nanoKAZ secretion. Labeled a and b represent the bright-field image and luminescence image of nanoKAZ from the stable expressed cell line, pcDNA3-GLsp-nanoKAZ/CHO-K1, respectively, and labeled c and d represent the bright-field image and luminescence image of nanoKAZ from the stable expressed cell line pcDNA3-nanoKAZ/CHO-K1, respectively.
Figure 5:
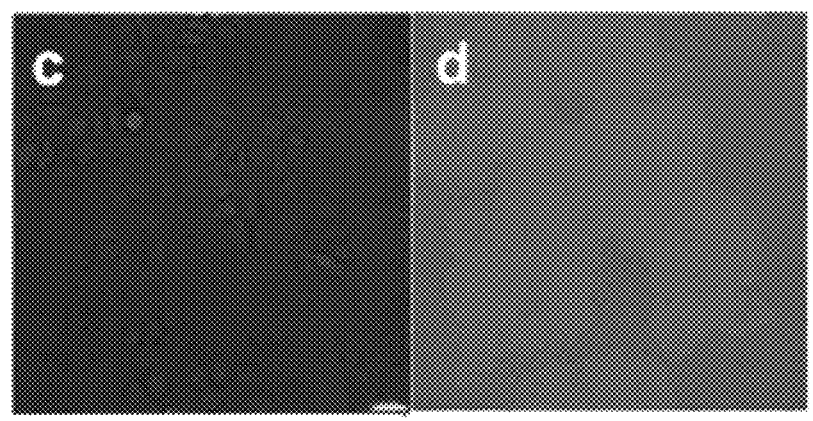

Using the stable expressed cell lines established in EXAMPLES 14 and 15, the visualization of nanoKAZ secretion was performed. The $10^4$ cells were cultured in a 35 mm glass bottom plate (manufactured by Iwaki Corp.) in 3 mL of MEM-alpha medium (manufactured by Wako Pure Chemical Industries, Ltd.) containing 10% FBS at 37° C. in a 5% $CO_2$ incubator for 48 hours. After washing 3 times with 3 mL of HBSS (manufactured by Wako Pure Chemical Industries, Ltd.), h-coelenterazine dissolved in HBSS at a final concentration of 3 µg/mL was added to cells. The visualized images were captured using an IX81-ZDC microscope (manufactured by Olympus Optical Co.) equipped with an EM-CCD camera (ImagEM 1K: manufactured by Hamamatsu Photonics K.K.) under image acquisition conditions (1×1 binning, fast scanning, EM-gain level 255, photon-counting level=1, image acquisition time, 0.5 sec.). After the addition of h-coelenterazine in 15 seconds, the captured images are shown in FIG. 5. Labeled a and b designate the bright-field image and the luminescence image of nanoKAZ from pcDNA3-GLsp-nanoKAZ/CHO-K1 stable expressed cells, respectively. Labeled c and d designate the bright-field image and the luminescence image of nanoKAZ from pcDNA3-nanoKAZ/CHO-K1 stable expression cells, respectively. Comparison between the luminescence images b and d obtained by the luminescence imaging indicate that, unlike nanoKAZ from the pcDNA3-GLsp-nanaKAZ/CHO-K1 cells secreted from the endoplasmic reticulum through the trans-Golgi network, nanaoKAZ from the pcDNA3-nanoKAZ/CHO-K1 cells were uniformly distributed on the cell surface and were secreted outside of cells, showing a different mode of secretion. More specifically, based on the results of experiments of amino-terminal deleted nanoKAZ gene expression in EXAMPLES 8 and 13, it was revealed that different secretion information from that of general secretory signal peptide sequences was found in the amino acid region at the positions of 1 to 4 from the amino terminus of nanoKAZ and, therefore, the visualized images of secretion were different as well.

Example 18

Substrate Specificities for Amino-Terminal Deleted nanoKAZ

The enzyme solutions of amino-terminal deleted nanoKAZ used for substrate specificity studies were prepared by the method described in EXAMPLE 12, using pcDNA3 vectors (pcDNA3-ΔN2T-nKAZ, pcDNA3-ΔN3L-nKAZ, pcDNA3-ΔN4E-nKAZ, pcDNA3-ΔN5D-nKAZ and pcDNA3-ΔN6F-nKAZ) for expression of the amino-terminal deletions, which were obtained by the method described in EXAMPLE 11. After transfection to CHO-K1 cells and then incubation for 48 hours, the culture medium were collected and stored in a frozen state. The coelenterazine analogues used for substrate specificity studies were synthesized by the methods described in publications, respectively. Specifically, coelenterazine (CTZ), h-coelenterazine (h-CTZ) and f-coelenterazine (f-CTZ), 6h-f-coelenterazine (6h-f-CTZ) were synthesized by the method described in Inouye et al (2013) Biochem. Biophys. Res. Commun, 437: 23-28, and bis-coelenterazine (bis-CTZ) was synthesized by the method described in Nakamura et al. (1997) Tetrahedron Lett, 38: 6405-6406.

A luminescence reaction was started by the addition of 2 µL of the freeze-thawed culture medium on ice to 100 µL of TE containing 1 µg of coelenterazine or its analogue. The luminescence activities were measured for 10 seconds using a luminometer (manufactured by Atto Inc.: AB2200), and the maximum intensity of luminescence ($I_{max}$) of nanoKAZ was shown as a relative luminescence activity using coelenterazine as a substrate. The results are shown in TABLE 5.

TABLE 5

| Deletion mutant | Relative luminescence activity ($I_{max}$) | | | | |
|---|---|---|---|---|---|
| | CTZ | bis-CTZ | 6h-f-CTZ | h-CTZ | f-CTZ |
| nanoKAZ | 1.00 | 6.93 | 7.00 | 11.76 | 12.65 |
| ΔN2T-nKAZ | 1.03 | 8.99 | 8.02 | 13.38 | 15.04 |
| ΔN3L-nKAZ | 0.50 | 5.39 | 5.25 | 9.39 | 9.88 |
| ΔN4E-nKAZ | 0.05 | 0.35 | 0.36 | 0.58 | 0.20 |

TABLE 5-continued

| Deletion mutant | Relative luminescence activity ($I_{max}$) | | | | |
|---|---|---|---|---|---|
| | CTZ | bis-CTZ | 6h-f-CTZ | h-CTZ | f-CTZ |
| ΔN5D-nKAZ | 0.01 | 0.01 | 0.01 | 0.01 | 0.02 |
| ΔN6F-nKAZ | less than 0.01 | less than 0.01 | less than 0.01 | less than 0.01 | less than 0.01 |

As shown in TABLE 5, when bis-CTZ, 6h-f-CTZ, h-CTZ and f-CTZ were used as substrates, the nanoKAZ deletion mutants of ΔN2T-nKAZ, ΔN3L-nKAZ and ΔN4E-nKAZ showed approximately 8 to 15-fold higher activity than coelenterazine (CTZ) used as the substrate. Particularly, h-CTZ and f-CTZ.showed over 10-fold higher activity than coeleneterazine. In addition, the nanoKAZ deletion mutant of ΔN2T-nKAZ was found to show a higher activity than nanoKAZ when bis-CTZ, 6h-f-CTZ, h-CTZ and f-CTZ were used.

[Sequence Listing Free Text]
[SEQ ID NO: 1] Nucleotide sequence of nanoKAZ
[SEQ ID NO: 2] Amino acid sequence of nanoKAZ
[SEQ ID NO: 3] Nucleotide sequence of ΔN2T-nKAZ
[SEQ ID NO: 4] Amino acid sequence of ΔN2T-nKAZ
[SEQ ID NO: 5] Nucleotide sequence of ΔN3L-nKAZ
[SEQ ID NO: 6] Amino acid sequence of ΔN3L-nKAZ
[SEQ ID NO: 7] Nucleotide sequence of ΔN4E-nKAZ
[SEQ ID NO: 8] Amino acid sequence of ΔN4E-nKAZ
[SEQ ID NO: 9] Nucleotide sequence of ΔN5D-nKAZ
[SEQ ID NO: 10] Amino acid sequence of ΔN5D-nK
[SEQ ID NO: 11] Nucleotide sequence of pCold-ZZ-P-nanoKAZ
[SEQ ID NO: 12] Amino acid sequence of pCold-ZZ-P-nanoKAZ
[SEQ ID NO: 13] Nucleotide sequence of pCold-nanoKAZ
[SEQ ID NO: 14] Amino acid sequence of pCold-nanoKAZ
[SEQ ID NO: 15] Nucleotide sequence of pcDNA3-GLsp-nanoKAZ
[SEQ ID NO: 16] Amino acid sequence of pcDNA3-GLsp-nanoKAZ
[SEQ ID NO: 17] Nucleotide sequence of pcDNA3-nanoKAZ
[SEQ ID NO: 18] Amino acid sequence of pcDNA3-nanoKAZ
[SEQ ID NO: 19] Nucleotide sequence of the primer used in EXAMPLES (nanoKAZ-1N/EcoRI)
[SEQ ID NO: 20] Nucleotide sequence of the primer used in EXAMPLES (nanoKAZ-3C/XbaI)
[SEQ ID NO: 21] Nucleotide sequence of the primer used in EXAMPLES (GLsp-1R/EcoRI)
[SEQ ID NO: 22] Nucleotide sequence of the primer used in EXAMPLES (T7 primer
[SEQ ID NO: 23] Nucleotide sequence of the primer used in EXAMPLES (D2-nKAZ-15N/EcoRI)
[SEQ ID NO: 24] Nucleotide sequence of the primer used in EXAMPLES (D3-nKAZ-16N/ECoRI)
[SEQ ID NO: 25] Nucleotide sequence of the primer used in EXAMPLES (D4-nKAZ-17N/EcoRI)
[SEQ ID NO: 26] Nucleotide sequence of the primer used in EXAMPLES (D5nanoKAZ-4N/EcoRI)
[SEQ ID NO: 27] Nucleotide sequence of the primer used in EXAMPLES (D6nanoKAZ-8N/EcoRI)
[SEQ ID NO: 28] Nucleotide sequence of the primer used in EXAMPLES (D7nanoKAZ-9N/EcoRI)
[SEQ ID NO: 29] Nucleotide sequence of the primer used in EXAMPLES (D8nanoKAZ-10N/EcoRI)
[SEQ ID NO: 30] Nucleotide sequence (D9nanoKAZ-11N/EcoRI) of the primer used in EXAMPLES
[SEQ ID NO: 31] Nucleotide sequence of the primer used in EXAMPLES (D10nanoKAZ-5N/EcoRI)
[SEQ ID NO: 32] Nucleotide sequence of the primer used in EXAMPLES (D15nanoKAZ-6N/EcoRI)
[SEQ ID NO: 33] Nucleotide sequence of the primer used in EXAMPLES (D20nanoKAZ-7N/EcoRI)

The invention claimed is:

1. A luciferase mutant selected from (a) to (d) below:
(a) a luciferase mutant consisting of an amino acid sequence in which at least one amino acid selected from amino acids at the positions of 1 to 4 is deleted in the amino acid sequence of SEQ ID NO: 2;
(b) a luciferase mutant consisting of an amino acid sequence in which at least one amino acid selected from amino acids at the positions of 1 to 4 is deleted in the amino acid sequence of SEQ ID NO: 2 and an amino acid sequence excluding the amino acids at the positions of 1 to 4 is an amino acid sequence in which 1 to 17 amino acids are deleted, substituted, inserted and/or added in the amino acid sequence at the positions of 5 to 169 of SEQ ID NO: 2, and having a luciferase activity;
(c) a luciferase mutant consisting of an amino acid sequence in which at least one amino acid selected from amino acids at the positions of 1 to 4 is deleted in the amino acid sequence of SEQ ID NO: 2 and an amino acid sequence excluding the amino acids at the positions of 1 to 4 has at least 90% identity to the amino acid sequence at the positions of 5 to 169 of SEQ ID NO: 2, and having a luciferase activity; and,
(d) a luciferase mutant consisting of an amino acid sequence in which at least one amino acid selected from amino acids at the positions of 1 to 4 is deleted in the amino acid sequence of SEQ ID NO: 2 and an amino acid sequence excluding the amino acids at the positions of 1 to 4 is encoded by a polynucleotide which hybridizes under stringent conditions to a polynucleotide consisting of a nucleotide sequence complementary to a nucleotide sequence encoding the amino acid sequence at the positions of 5 to 169 of SEQ ID NO: 2, wherein the high stringency conditions are 5 × SSC, 5 × Denhardt's solution, 0.5% (w/v) SDS, 50% (v/v) formamide, and 50° C., and having a luciferase activity.

2. The luciferase mutant according to claim 1, wherein the luciferase mutants defined in (b) to (d) above are mutants defined in (b-1) to (d-1) below:
(b-1) a luciferase mutant consisting of an amino acid sequence in which at least one amino acid selected from amino acids at the positions of 1 to 4 is deleted in the amino acid sequence of SEQ ID NO: 2 and an amino acid sequence excluding the amino acids at the positions of 1 to 4 is an amino acid sequence in which 1 to 9 amino acids are deleted, substituted, inserted and/or added in the amino acid sequence at the positions of 5 to 169 of SEQ ID NO: 2, and having a luciferase activity;
(c-1) a luciferase mutant consisting of an amino acid sequence in which at least one amino acid selected from amino acids at the positions of 1 to 4 is deleted in the amino acid sequence of SEQ ID NO: 2 and an amino acid sequence excluding the amino acids at the positions of 1 to 4 has at least 95% identity to the amino acid sequence at the positions of 5 to 169 of SEQ ID NO: 2, and having a luciferase activity; and,
(d-1) a luciferase mutant consisting of an amino acid sequence in which at least one amino acid selected from amino acids at the positions of 1 to 4 is deleted in the amino acid sequence of SEQ ID NO: 2 and an amino acid sequence excluding the amino acids at the positions of 1 to 4 is encoded by a polynucleotide which hybridizes under high stringent conditions to a polynucleotide consisting of a nucleotide sequence complementary to a nucleotide sequence encoding the amino acid sequence at the positions of 5 to 169 of SEQ ID NO: 2, wherein the high stringency conditions are 5 × SC, 5 × Denhardt's solution, 0.5% (w/v) SDS, 50% (v/v) formamide, and 50° C., and having a luciferase activity.

3. A luciferase mutant consisting of an amino acid sequence selected from SEQ ID NO: 4, SEQ ID NO: 6, SEQ ID NO: 8 and SEQ ID NO: 10.

4. A kit comprising the luciferase mutant according to claim 1.

5. The kit according to claim 4, further comprising a luciferin.

6. The kit according to claim 5, wherein the luciferin is coelenterazines.

7. The kit according to claim 6, wherein the coelenterazines is bis-coelenterazine or 6h-f-coelenterazine.

8. A kit comprising the luciferase mutant according to claim 2.

9. The kit according to claim 8, further comprising a luciferin.

10. The kit according to claim 9, wherein the luciferin is coelenterazines.

11. The kit according to claim 10, wherein the coelenterazines is bis-coelenterazine or 6h-f-coelenterazine.

12. A kit comprising the luciferase mutant according to claim 3.

13. The kit according to claim 12, further comprising a luciferin.

14. The kit according to claim 13, wherein the luciferin is coelenterazines.

15. The kit according to claim 14, wherein the coelenterazines is bis-coelenterazine or 6h-f-coelenterazine.

\* \* \* \* \*

SEQUENCE LISTING

```
<160> NUMBER OF SEQ ID NOS: 33

<210> SEQ ID NO 1
<211> LENGTH: 510
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(510)

<400> SEQUENCE: 1 ttc acc ctg gag gac ttc gtc ggc gac tgg aga cag acc gcc ggc tac      48
Phe Thr Leu Glu Asp Phe Val Gly Asp Trp Arg Gln Thr Ala Gly Tyr
1               5                   10                  15 aac ctg gac cag gtc ctg gag cag ggc ggc gtc agc agc ctg ttc cag      96
Asn Leu Asp Gln Val Leu Glu Gln Gly Gly Val Ser Ser Leu Phe Gln
            20                  25                  30 aac ctg ggc gtc agc gtc acc ccc atc cag aga atc gtc ctt agc ggc     144
Asn Leu Gly Val Ser Val Thr Pro Ile Gln Arg Ile Val Leu Ser Gly
        35                  40                  45 gag aac ggc ctg aag atc gac atc cac gtc atc atc ccc tac gag ggc     192
Glu Asn Gly Leu Lys Ile Asp Ile His Val Ile Ile Pro Tyr Glu Gly
    50                  55                  60
```

```
ctg agc ggc gac cag atg ggc cag atc gag aag atc ttc aag gtc gtc      240
Leu Ser Gly Asp Gln Met Gly Gln Ile Glu Lys Ile Phe Lys Val Val
 65              70                  75                  80 tac ccc gtc gac gac cac cac ttc aag gtc atc ctg cac tac ggc acc      288
Tyr Pro Val Asp Asp His His Phe Lys Val Ile Leu His Tyr Gly Thr
             85                  90                  95 ctg gtc atc gac ggc gtc acc ccc aac atg atc gac tac ttc ggt aga      336
Leu Val Ile Asp Gly Val Thr Pro Asn Met Ile Asp Tyr Phe Gly Arg
         100                 105                 110 ccc tac gag ggc atc gcc gtc ttc gac ggc aag aag atc acc gtc acc      384
Pro Tyr Glu Gly Ile Ala Val Phe Asp Gly Lys Lys Ile Thr Val Thr
     115                 120                 125 ggc acc ctg tgg aac ggc aac aag atc atc gac gag aga ctg atc aac      432
Gly Thr Leu Trp Asn Gly Asn Lys Ile Ile Asp Glu Arg Leu Ile Asn
130                 135                 140 ccc gac ggc agc ctg ctg ttc aga gtc acc atc aac ggc gtc acc ggc      480
Pro Asp Gly Ser Leu Leu Phe Arg Val Thr Ile Asn Gly Val Thr Gly
145                 150                 155                 160 tgg aga ctg tgc gag aga atc ctg gcc taa                              510
Trp Arg Leu Cys Glu Arg Ile Leu Ala
                165

<210> SEQ ID NO 2
<211> LENGTH: 169
<212> TYPE: PRT
<213> ORGANISM: Artificial sequence
<220> FEATURE:
<223> OTHER INFORMATION: Synthetic Construct

<400> SEQUENCE: 2

Phe Thr Leu Glu Asp Phe Val Gly Asp Trp Arg Gln Thr Ala Gly Tyr
 1               5                  10                  15

Asn Leu Asp Gln Val Leu Glu Gln Gly Gly Val Ser Ser Leu Phe Gln
             20                  25                  30

Asn Leu Gly Val Ser Val Thr Pro Ile Gln Arg Ile Val Leu Ser Gly
         35                  40                  45

Glu Asn Gly Leu Lys Ile Asp Ile His Val Ile Pro Tyr Glu Gly
     50                  55                  60

Leu Ser Gly Asp Gln Met Gly Gln Ile Glu Lys Ile Phe Lys Val Val
 65              70                  75                  80

Tyr Pro Val Asp Asp His His Phe Lys Val Ile Leu His Tyr Gly Thr
             85                  90                  95

Leu Val Ile Asp Gly Val Thr Pro Asn Met Ile Asp Tyr Phe Gly Arg
         100                 105                 110

Pro Tyr Glu Gly Ile Ala Val Phe Asp Gly Lys Lys Ile Thr Val Thr
     115                 120                 125

Gly Thr Leu Trp Asn Gly Asn Lys Ile Ile Asp Glu Arg Leu Ile Asn
130                 135                 140

Pro Asp Gly Ser Leu Leu Phe Arg Val Thr Ile Asn Gly Val Thr Gly
145                 150                 155                 160

Trp Arg Leu Cys Glu Arg Ile Leu Ala
                165

<210> SEQ ID NO 3
<211> LENGTH: 507
<212> TYPE: DNA
<213> ORGANISM: Artificial sequence
<220> FEATURE:
<223> OTHER INFORMATION: synthetic DNA
```

```
<220> FEATURE:
<221> NAME/KEY: CDS
<222> LOCATION: (1)..(507)

<400> SEQUENCE: 3 acc ctg gag gac ttc gtc ggc gac tgg aga cag acc gcc ggc tac aac      48
Thr Leu Glu Asp Phe Val Gly Asp Trp Arg Gln Thr Ala Gly Tyr Asn
1               5                   10                  15 ctg gac cag gtc ctg gag cag ggc ggc gtc agc agc ctg ttc cag aac      96
Leu Asp Gln Val Leu Glu Gln Gly Gly Val Ser Ser Leu Phe Gln Asn
            20                  25                  30 ctg ggc gtc agc gtc acc ccc atc cag aga atc gtc ctt agc ggc gag     144
Leu Gly Val Ser Val Thr Pro Ile Gln Arg Ile Val Leu Ser Gly Glu
        35                  40                  45 aac ggc ctg aag atc gac atc cac gtc atc atc ccc tac gag ggc ctg     192
Asn Gly Leu Lys Ile Asp Ile His Val Ile Ile Pro Tyr Glu Gly Leu
50                  55                  60 agc ggc gac cag atg ggc cag atc gag aag atc ttc aag gtc gtc tac     240
Ser Gly Asp Gln Met Gly Gln Ile Glu Lys Ile Phe Lys Val Val Tyr
65                  70                  75                  80 ccc gtc gac gac cac cac ttc aag gtc atc ctg cac tac ggc acc ctg     288
Pro Val Asp Asp His His Phe Lys Val Ile Leu His Tyr Gly Thr Leu
                85                  90                  95 gtc atc gac ggc gtc acc ccc aac atg atc gac tac ttc ggt aga ccc     336
Val Ile Asp Gly Val Thr Pro Asn Met Ile Asp Tyr Phe Gly Arg Pro
            100                 105                 110 tac gag ggc atc gcc gtc ttc gac ggc aag aag atc acc gtc acc ggc     384
Tyr Glu Gly Ile Ala Val Phe Asp Gly Lys Lys Ile Thr Val Thr Gly
        115                 120                 125 acc ctg tgg aac ggc aac aag atc atc gac gag aga ctg atc aac ccc     432
Thr Leu Trp Asn Gly Asn Lys Ile Ile Asp Glu Arg Leu Ile Asn Pro
    130                 135                 140 gac ggc agc ctg ctg ttc aga gtc acc atc aac ggc gtc acc ggc tgg     480
Asp Gly Ser Leu Leu Phe Arg Val Thr Ile Asn Gly Val Thr Gly Trp
145                 150                 155                 160 aga ctg tgc gag aga atc ctg gcc taa                                 507
Arg Leu Cys Glu Arg Ile Leu Ala
                165

<210> SEQ ID NO 4
<211> LENGTH: 168
<212> TYPE: PRT
<213> ORGANISM: Artificial sequence
<220> FEATURE:
<223> OTHER INFORMATION: Synthetic Construct

<400> SEQUENCE: 4

Thr Leu Glu Asp Phe Val Gly Asp Trp Arg Gln Thr Ala Gly Tyr Asn
1               5                   10                  15

Leu Asp Gln Val Leu Glu Gln Gly Gly Val Ser Ser Leu Phe Gln Asn
            20                  25                  30

Leu Gly Val Ser Val Thr Pro Ile Gln Arg Ile Val Leu Ser Gly Glu
        35                  40                  45

Asn Gly Leu Lys Ile Asp Ile His Val Ile Ile Pro Tyr Glu Gly Leu
50                  55                  60

Ser Gly Asp Gln Met Gly Gln Ile Glu Lys Ile Phe Lys Val Val Tyr
65                  70                  75                  80

Pro Val Asp Asp His His Phe Lys Val Ile Leu His Tyr Gly Thr Leu
                85                  90                  95

Val Ile Asp Gly Val Thr Pro Asn Met Ile Asp Tyr Phe Gly Arg Pro
```

```
                    100                 105                 110
Tyr Glu Gly Ile Ala Val Phe Asp Gly Lys Lys Ile Thr Val Thr Gly
            115                 120                 125

Thr Leu Trp Asn Gly Asn Lys Ile Ile Asp Glu Arg Leu Ile Asn Pro
    130                 135                 140

Asp Gly Ser Leu Leu Phe Arg Val Thr Ile Asn Gly Val Thr Gly Trp
145                 150                 155                 160

Arg Leu Cys Glu Arg Ile Leu Ala
                165

<210> SEQ ID NO 5
<211> LENGTH: 504
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(504)

<400> SEQUENCE: 5 ctg gag gac ttc gtc ggc gac tgg aga cag acc gcc ggc tac aac ctg       48
Leu Glu Asp Phe Val Gly Asp Trp Arg Gln Thr Ala Gly Tyr Asn Leu
1               5                   10                  15 gac cag gtc ctg gag cag ggc ggc gtc agc agc ctg ttc cag aac ctg       96
Asp Gln Val Leu Glu Gln Gly Gly Val Ser Ser Leu Phe Gln Asn Leu
            20                  25                  30 ggc gtc agc gtc acc ccc atc cag aga atc gtc ctt agc ggc gag aac      144
Gly Val Ser Val Thr Pro Ile Gln Arg Ile Val Leu Ser Gly Glu Asn
        35                  40                  45 ggc ctg aag atc gac atc cac gtc atc atc ccc tac gag ggc ctg agc      192
Gly Leu Lys Ile Asp Ile His Val Ile Ile Pro Tyr Glu Gly Leu Ser
    50                  55                  60 ggc gac cag atg ggc cag atc gag aag atc ttc aag gtc gtc tac ccc      240
Gly Asp Gln Met Gly Gln Ile Glu Lys Ile Phe Lys Val Val Tyr Pro
65                  70                  75                  80 gtc gac gac cac cac ttc aag gtc atc ctg cac tac ggc acc ctg gtc      288
Val Asp Asp His His Phe Lys Val Ile Leu His Tyr Gly Thr Leu Val
                85                  90                  95 atc gac ggc gtc acc ccc aac atg atc gac tac ttc ggt aga ccc tac      336
Ile Asp Gly Val Thr Pro Asn Met Ile Asp Tyr Phe Gly Arg Pro Tyr
            100                 105                 110 gag ggc atc gcc gtc ttc gac ggc aag aag atc acc gtc acc ggc acc      384
Glu Gly Ile Ala Val Phe Asp Gly Lys Lys Ile Thr Val Thr Gly Thr
        115                 120                 125 ctg tgg aac ggc aac aag atc atc gac gag aga ctg atc aac ccc gac      432
Leu Trp Asn Gly Asn Lys Ile Ile Asp Glu Arg Leu Ile Asn Pro Asp
    130                 135                 140 ggc agc ctg ctg ttc aga gtc acc atc aac ggc gtc acc ggc tgg aga      480
Gly Ser Leu Leu Phe Arg Val Thr Ile Asn Gly Val Thr Gly Trp Arg
145                 150                 155                 160 ctg tgc gag aga atc ctg gcc taa                                      504
Leu Cys Glu Arg Ile Leu Ala
                165

<210> SEQ ID NO 6
<211> LENGTH: 167
<212> TYPE: PRT
<213> ORGANISM: Artificial sequence
<220> FEATURE:
<223> OTHER INFORMATION: Synthetic Construct
```

```
<400> SEQUENCE: 6

Leu Glu Asp Phe Val Gly Asp Trp Arg Gln Thr Ala Gly Tyr Asn Leu
1               5                   10                  15

Asp Gln Val Leu Glu Gln Gly Gly Val Ser Ser Leu Phe Gln Asn Leu
            20                  25                  30

Gly Val Ser Val Thr Pro Ile Gln Arg Ile Val Leu Ser Gly Glu Asn
        35                  40                  45

Gly Leu Lys Ile Asp Ile His Val Ile Ile Pro Tyr Glu Gly Leu Ser
    50                  55                  60

Gly Asp Gln Met Gly Gln Ile Glu Lys Ile Phe Lys Val Val Tyr Pro
65                  70                  75                  80

Val Asp Asp His His Phe Lys Val Ile Leu His Tyr Gly Thr Leu Val
                85                  90                  95

Ile Asp Gly Val Thr Pro Asn Met Ile Asp Tyr Phe Gly Arg Pro Tyr
            100                 105                 110

Glu Gly Ile Ala Val Phe Asp Gly Lys Lys Ile Thr Val Thr Gly Thr
        115                 120                 125

Leu Trp Asn Gly Asn Lys Ile Ile Asp Glu Arg Leu Ile Asn Pro Asp
    130                 135                 140

Gly Ser Leu Leu Phe Arg Val Thr Ile Asn Gly Val Thr Gly Trp Arg
145                 150                 155                 160

Leu Cys Glu Arg Ile Leu Ala
                165

<210> SEQ ID NO 7
<211> LENGTH: 501
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(501)

<400> SEQUENCE: 7 gag gac ttc gtc ggc gac tgg aga cag acc gcc ggc tac aac ctg gac       48
Glu Asp Phe Val Gly Asp Trp Arg Gln Thr Ala Gly Tyr Asn Leu Asp
1               5                   10                  15 cag gtc ctg gag cag ggc ggc gtc agc agc ctg ttc cag aac ctg ggc       96
Gln Val Leu Glu Gln Gly Gly Val Ser Ser Leu Phe Gln Asn Leu Gly
            20                  25                  30 gtc agc gtc acc ccc atc cag aga atc gtc ctt agc ggc gag aac ggc      144
Val Ser Val Thr Pro Ile Gln Arg Ile Val Leu Ser Gly Glu Asn Gly
        35                  40                  45 ctg aag atc gac atc cac gtc atc atc ccc tac gag ggc ctg agc ggc      192
Leu Lys Ile Asp Ile His Val Ile Ile Pro Tyr Glu Gly Leu Ser Gly
    50                  55                  60 gac cag atg ggc cag atc gag aag atc ttc aag gtc gtc tac ccc gtc      240
Asp Gln Met Gly Gln Ile Glu Lys Ile Phe Lys Val Val Tyr Pro Val
65                  70                  75                  80 gac gac cac cac ttc aag gtc atc ctg cac tac ggc acc ctg gtc atc      288
Asp Asp His His Phe Lys Val Ile Leu His Tyr Gly Thr Leu Val Ile
                85                  90                  95 gac ggc gtc acc ccc aac atg atc gac tac ttc ggt aga ccc tac gag      336
Asp Gly Val Thr Pro Asn Met Ile Asp Tyr Phe Gly Arg Pro Tyr Glu
            100                 105                 110 ggc atc gcc gtc ttc gac ggc aag aag atc acc gtc acc ggc acc ctg      384
Gly Ile Ala Val Phe Asp Gly Lys Lys Ile Thr Val Thr Gly Thr Leu
        115                 120                 125
```

```
tgg aac ggc aac aag atc atc gac gag aga ctg atc aac ccc gac ggc      432
Trp Asn Gly Asn Lys Ile Ile Asp Glu Arg Leu Ile Asn Pro Asp Gly
        130                 135                 140 agc ctg ctg ttc aga gtc acc atc aac ggc gtc acc ggc tgg aga ctg      480
Ser Leu Leu Phe Arg Val Thr Ile Asn Gly Val Thr Gly Trp Arg Leu
145                 150                 155                 160 tgc gag aga atc ctg gcc taa                                          501
Cys Glu Arg Ile Leu Ala
                165

<210> SEQ ID NO 8
<211> LENGTH: 166
<212> TYPE: PRT
<213> ORGANISM: Artificial sequence
<220> FEATURE:
<223> OTHER INFORMATION: Synthetic Construct

<400> SEQUENCE: 8

Glu Asp Phe Val Gly Asp Trp Arg Gln Thr Ala Gly Tyr Asn Leu Asp
1               5                   10                  15

Gln Val Leu Glu Gln Gly Gly Val Ser Ser Leu Phe Gln Asn Leu Gly
            20                  25                  30

Val Ser Val Thr Pro Ile Gln Arg Ile Val Leu Ser Gly Glu Asn Gly
        35                  40                  45

Leu Lys Ile Asp Ile His Val Ile Ile Pro Tyr Glu Gly Leu Ser Gly
    50                  55                  60

Asp Gln Met Gly Gln Ile Glu Lys Ile Phe Lys Val Val Tyr Pro Val
65                  70                  75                  80

Asp Asp His His Phe Lys Val Ile Leu His Tyr Gly Thr Leu Val Ile
                85                  90                  95

Asp Gly Val Thr Pro Asn Met Ile Asp Tyr Phe Gly Arg Pro Tyr Glu
            100                 105                 110

Gly Ile Ala Val Phe Asp Gly Lys Lys Ile Thr Val Thr Gly Thr Leu
        115                 120                 125

Trp Asn Gly Asn Lys Ile Ile Asp Glu Arg Leu Ile Asn Pro Asp Gly
    130                 135                 140

Ser Leu Leu Phe Arg Val Thr Ile Asn Gly Val Thr Gly Trp Arg Leu
145                 150                 155                 160

Cys Glu Arg Ile Leu Ala
                165

<210> SEQ ID NO 9
<211> LENGTH: 498
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(498)

<400> SEQUENCE: 9 gac ttc gtc ggc gac tgg aga cag acc gcc ggc tac aac ctg gac cag      48
Asp Phe Val Gly Asp Trp Arg Gln Thr Ala Gly Tyr Asn Leu Asp Gln
1               5                   10                  15 gtc ctg gag cag ggc ggc gtc agc agc ctg ttc cag aac ctg ggc gtc      96
Val Leu Glu Gln Gly Gly Val Ser Ser Leu Phe Gln Asn Leu Gly Val
            20                  25                  30 agc gtc acc ccc atc cag aga atc gtc ctt agc ggc gag aac ggc ctg      144
Ser Val Thr Pro Ile Gln Arg Ile Val Leu Ser Gly Glu Asn Gly Leu
```

```
              35                  40                  45
aag atc gac atc cac gtc atc atc ccc tac gag ggc ctg agc ggc gac    192
Lys Ile Asp Ile His Val Ile Ile Pro Tyr Glu Gly Leu Ser Gly Asp
     50                  55                  60 cag atg ggc cag atc gag aag atc ttc aag gtc gtc tac ccc gtc gac    240
Gln Met Gly Gln Ile Glu Lys Ile Phe Lys Val Val Tyr Pro Val Asp
 65                  70                  75                  80 gac cac cac ttc aag gtc atc ctg cac tac ggc acc ctg gtc atc gac    288
Asp His His Phe Lys Val Ile Leu His Tyr Gly Thr Leu Val Ile Asp
                 85                  90                  95 ggc gtc acc ccc aac atg atc gac tac ttc ggt aga ccc tac gag ggc    336
Gly Val Thr Pro Asn Met Ile Asp Tyr Phe Gly Arg Pro Tyr Glu Gly
            100                 105                 110 atc gcc gtc ttc gac ggc aag aag atc acc gtc acc ggc acc ctg tgg    384
Ile Ala Val Phe Asp Gly Lys Lys Ile Thr Val Thr Gly Thr Leu Trp
        115                 120                 125 aac ggc aac aag atc atc gac gag aga ctg atc aac ccc gac ggc agc    432
Asn Gly Asn Lys Ile Ile Asp Glu Arg Leu Ile Asn Pro Asp Gly Ser
130                 135                 140 ctg ctg ttc aga gtc acc atc aac ggc gtc acc ggc tgg aga ctg tgc    480
Leu Leu Phe Arg Val Thr Ile Asn Gly Val Thr Gly Trp Arg Leu Cys
145                 150                 155                 160 gag aga atc ctg gcc taa                                            498
Glu Arg Ile Leu Ala
            165
```

<210> SEQ ID NO 10
<211> LENGTH: 165
<212> TYPE: PRT
<213> ORGANISM: Artificial sequence
<220> FEATURE:
<223> OTHER INFORMATION: Synthetic Construct

<400> SEQUENCE: 10

```
Asp Phe Val Gly Asp Trp Arg Gln Thr Ala Gly Tyr Asn Leu Asp Gln
 1               5                  10                  15

Val Leu Glu Gln Gly Gly Val Ser Ser Leu Phe Gln Asn Leu Gly Val
            20                  25                  30

Ser Val Thr Pro Ile Gln Arg Ile Val Leu Ser Gly Glu Asn Gly Leu
        35                  40                  45

Lys Ile Asp Ile His Val Ile Ile Pro Tyr Glu Gly Leu Ser Gly Asp
     50                  55                  60

Gln Met Gly Gln Ile Glu Lys Ile Phe Lys Val Val Tyr Pro Val Asp
 65                  70                  75                  80

Asp His His Phe Lys Val Ile Leu His Tyr Gly Thr Leu Val Ile Asp
                 85                  90                  95

Gly Val Thr Pro Asn Met Ile Asp Tyr Phe Gly Arg Pro Tyr Glu Gly
            100                 105                 110

Ile Ala Val Phe Asp Gly Lys Lys Ile Thr Val Thr Gly Thr Leu Trp
        115                 120                 125

Asn Gly Asn Lys Ile Ile Asp Glu Arg Leu Ile Asn Pro Asp Gly Ser
130                 135                 140

Leu Leu Phe Arg Val Thr Ile Asn Gly Val Thr Gly Trp Arg Leu Cys
145                 150                 155                 160

Glu Arg Ile Leu Ala
            165
```

<210> SEQ ID NO 11

<211> LENGTH: 990
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(990)

<400> SEQUENCE: 11

```
atg aat cac aaa gtg cat cat cat cat cat cat atg gcg caa cac gat      48
Met Asn His Lys Val His His His His His His Met Ala Gln His Asp
1               5                  10                  15 gaa gcc gta gac aac aaa ttc aac aaa gaa caa caa aac gcg ttc tat      96
Glu Ala Val Asp Asn Lys Phe Asn Lys Glu Gln Gln Asn Ala Phe Tyr
            20                  25                  30 gag atc tta cat tta cct aac tta aac gaa gaa caa cga aac gcc ttc     144
Glu Ile Leu His Leu Pro Asn Leu Asn Glu Glu Gln Arg Asn Ala Phe
        35                  40                  45 atc caa agt tta aaa gat gac cca agc caa agc gct aac ctt tta gca     192
Ile Gln Ser Leu Lys Asp Asp Pro Ser Gln Ser Ala Asn Leu Leu Ala
    50                  55                  60 gaa gct aaa aag cta aat gat gct cag gcg ccg aaa gta gac aac aaa     240
Glu Ala Lys Lys Leu Asn Asp Ala Gln Ala Pro Lys Val Asp Asn Lys
65                  70                  75                  80 ttc aac aaa gaa caa caa aac gcg ttc tat gag atc tta cat tta cct     288
Phe Asn Lys Glu Gln Gln Asn Ala Phe Tyr Glu Ile Leu His Leu Pro
                85                  90                  95 aac tta aac gaa gaa caa cga aac gcc ttc atc caa agt tta aaa gat     336
Asn Leu Asn Glu Glu Gln Arg Asn Ala Phe Ile Gln Ser Leu Lys Asp
            100                 105                 110 gac cca agc caa agc gct aac ctt tta gca gaa gct aaa aag cta aat     384
Asp Pro Ser Gln Ser Ala Asn Leu Leu Ala Glu Ala Lys Lys Leu Asn
        115                 120                 125 gat gct cag gcg ccg aaa gta gac gca aat tcg agc tcg gga tct ctg     432
Asp Ala Gln Ala Pro Lys Val Asp Ala Asn Ser Ser Ser Gly Ser Leu
    130                 135                 140 gaa gtt ctg ttc cag ggg ccc gaa ttc aag ctt ggt acc acc atg gtc     480
Glu Val Leu Phe Gln Gly Pro Glu Phe Lys Leu Gly Thr Thr Met Val
145                 150                 155                 160 ttc acc ctg gag gac ttc gtc ggc gac tgg aga cag acc gcc ggc tac     528
Phe Thr Leu Glu Asp Phe Val Gly Asp Trp Arg Gln Thr Ala Gly Tyr
                165                 170                 175 aac ctg gac cag gtc ctg gag cag ggc ggc gtc agc agc ctg ttc cag     576
Asn Leu Asp Gln Val Leu Glu Gln Gly Gly Val Ser Ser Leu Phe Gln
            180                 185                 190 aac ctg ggc gtc agc gtc acc ccc atc cag aga atc gtc ctt agc ggc     624
Asn Leu Gly Val Ser Val Thr Pro Ile Gln Arg Ile Val Leu Ser Gly
        195                 200                 205 gag aac ggc ctg aag atc gac atc cac gtc atc atc ccc tac gag ggc     672
Glu Asn Gly Leu Lys Ile Asp Ile His Val Ile Ile Pro Tyr Glu Gly
    210                 215                 220 ctg agc ggc gac cag atg ggc cag atc gag aag atc ttc aag gtc gtc     720
Leu Ser Gly Asp Gln Met Gly Gln Ile Glu Lys Ile Phe Lys Val Val
225                 230                 235                 240 tac ccc gtc gac gac cac cac ttc aag gtc atc ctg cac tac ggc acc     768
Tyr Pro Val Asp Asp His His Phe Lys Val Ile Leu His Tyr Gly Thr
                245                 250                 255 ctg gtc atc gac ggc gtc acc ccc aac atg atc gac tac ttc ggt aga     816
Leu Val Ile Asp Gly Val Thr Pro Asn Met Ile Asp Tyr Phe Gly Arg
            260                 265                 270
```

```
ccc tac gag ggc atc gcc gtc ttc gac ggc aag aag atc acc gtc acc    864
Pro Tyr Glu Gly Ile Ala Val Phe Asp Gly Lys Lys Ile Thr Val Thr
        275                 280                 285 ggc acc ctg tgg aac ggc aac aag atc atc gac gag aga ctg atc aac    912
Gly Thr Leu Trp Asn Gly Asn Lys Ile Ile Asp Glu Arg Leu Ile Asn
290                 295                 300 ccc gac ggc agc ctg ctg ttc aga gtc acc atc aac ggc gtc acc ggc    960
Pro Asp Gly Ser Leu Leu Phe Arg Val Thr Ile Asn Gly Val Thr Gly
305                 310                 315                 320 tgg aga ctg tgc gag aga atc ctg gcc taa                            990
Trp Arg Leu Cys Glu Arg Ile Leu Ala
                325
```

<210> SEQ ID NO 12
<211> LENGTH: 329
<212> TYPE: PRT
<213> ORGANISM: Artificial sequence
<220> FEATURE:
<223> OTHER INFORMATION: Synthetic Construct

<400> SEQUENCE: 12

```
Met Asn His Lys Val His His His His His Met Ala Gln His Asp
1               5                   10                  15

Glu Ala Val Asp Asn Lys Phe Asn Lys Glu Gln Gln Asn Ala Phe Tyr
            20                  25                  30

Glu Ile Leu His Leu Pro Asn Leu Asn Glu Glu Gln Arg Asn Ala Phe
            35                  40                  45

Ile Gln Ser Leu Lys Asp Asp Pro Ser Gln Ser Ala Asn Leu Leu Ala
        50                  55                  60

Glu Ala Lys Lys Leu Asn Asp Ala Gln Ala Pro Lys Val Asp Asn Lys
65                  70                  75                  80

Phe Asn Lys Glu Gln Gln Asn Ala Phe Tyr Glu Ile Leu His Leu Pro
                85                  90                  95

Asn Leu Asn Glu Glu Gln Arg Asn Ala Phe Ile Gln Ser Leu Lys Asp
            100                 105                 110

Asp Pro Ser Gln Ser Ala Asn Leu Leu Ala Glu Ala Lys Lys Leu Asn
        115                 120                 125

Asp Ala Gln Ala Pro Lys Val Asp Ala Asn Ser Ser Ser Gly Ser Leu
130                 135                 140

Glu Val Leu Phe Gln Gly Pro Glu Phe Lys Leu Gly Thr Thr Met Val
145                 150                 155                 160

Phe Thr Leu Glu Asp Phe Val Gly Asp Trp Arg Gln Thr Ala Gly Tyr
                165                 170                 175

Asn Leu Asp Gln Val Leu Glu Gln Gly Gly Val Ser Ser Leu Phe Gln
            180                 185                 190

Asn Leu Gly Val Ser Val Thr Pro Ile Gln Arg Ile Val Leu Ser Gly
        195                 200                 205

Glu Asn Gly Leu Lys Ile Asp Ile His Val Ile Pro Tyr Glu Gly
210                 215                 220

Leu Ser Gly Asp Gln Met Gly Gln Ile Glu Lys Ile Phe Lys Val Val
225                 230                 235                 240

Tyr Pro Val Asp Asp His His Phe Lys Val Ile Leu His Tyr Gly Thr
                245                 250                 255

Leu Val Ile Asp Gly Val Thr Pro Asn Met Ile Asp Tyr Phe Gly Arg
            260                 265                 270

Pro Tyr Glu Gly Ile Ala Val Phe Asp Gly Lys Lys Ile Thr Val Thr
        275                 280                 285
```

Gly Thr Leu Trp Asn Gly Asn Lys Ile Ile Asp Glu Arg Leu Ile Asn
    290                 295                 300

Pro Asp Gly Ser Leu Leu Phe Arg Val Thr Ile Asn Gly Val Thr Gly
305                 310                 315                 320

Trp Arg Leu Cys Glu Arg Ile Leu Ala
            325

<210> SEQ ID NO 13
<211> LENGTH: 513
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(513)

<400> SEQUENCE: 13

| atg gtc ttc acc ctg gag gac ttc gtc ggc gac tgg aga cag acc gcc | 48 |
|---|---|
| Met Val Phe Thr Leu Glu Asp Phe Val Gly Asp Trp Arg Gln Thr Ala | |
| 1               5                   10                  15 | |

| ggc tac aac ctg gac cag gtc ctg gag cag ggc ggc gtc agc agc ctg | 96 |
|---|---|
| Gly Tyr Asn Leu Asp Gln Val Leu Glu Gln Gly Gly Val Ser Ser Leu | |
|         20                  25                  30 | |

| ttc cag aac ctg ggc gtc agc gtc acc ccc atc cag aga atc gtc ctt | 144 |
|---|---|
| Phe Gln Asn Leu Gly Val Ser Val Thr Pro Ile Gln Arg Ile Val Leu | |
|     35                  40                  45 | |

| agc ggc gag aac ggc ctg aag atc gac atc cac gtc atc atc ccc tac | 192 |
|---|---|
| Ser Gly Glu Asn Gly Leu Lys Ile Asp Ile His Val Ile Ile Pro Tyr | |
| 50                  55                  60 | |

| gag ggc ctg agc ggc gac cag atg ggc cag atc gag aag atc ttc aag | 240 |
|---|---|
| Glu Gly Leu Ser Gly Asp Gln Met Gly Gln Ile Glu Lys Ile Phe Lys | |
| 65                  70                  75                  80 | |

| gtc gtc tac ccc gtc gac gac cac cac ttc aag gtc atc ctg cac tac | 288 |
|---|---|
| Val Val Tyr Pro Val Asp Asp His His Phe Lys Val Ile Leu His Tyr | |
|             85                  90                  95 | |

| ggc acc ctg gtc atc gac ggc gtc acc ccc aac atg atc gac tac ttc | 336 |
|---|---|
| Gly Thr Leu Val Ile Asp Gly Val Thr Pro Asn Met Ile Asp Tyr Phe | |
|         100                 105                 110 | |

| ggt aga ccc tac gag ggc atc gcc gtc ttc gac ggc aag aag atc acc | 384 |
|---|---|
| Gly Arg Pro Tyr Glu Gly Ile Ala Val Phe Asp Gly Lys Lys Ile Thr | |
|     115                 120                 125 | |

| gtc acc ggc acc ctg tgg aac ggc aac aag atc atc gac gag aga ctg | 432 |
|---|---|
| Val Thr Gly Thr Leu Trp Asn Gly Asn Lys Ile Ile Asp Glu Arg Leu | |
| 130                 135                 140 | |

| atc aac ccc gac ggc agc ctg ctg ttc aga gtc acc atc aac ggc gtc | 480 |
|---|---|
| Ile Asn Pro Asp Gly Ser Leu Leu Phe Arg Val Thr Ile Asn Gly Val | |
| 145                 150                 155                 160 | |

| acc ggc tgg aga ctg tgc gag aga atc ctg gcc | 513 |
|---|---|
| Thr Gly Trp Arg Leu Cys Glu Arg Ile Leu Ala | |
|             165                 170 | |

<210> SEQ ID NO 14
<211> LENGTH: 171
<212> TYPE: PRT
<213> ORGANISM: Artificial sequence
<220> FEATURE:
<223> OTHER INFORMATION: Synthetic Construct

<400> SEQUENCE: 14

Met Val Phe Thr Leu Glu Asp Phe Val Gly Asp Trp Arg Gln Thr Ala
1               5                   10                  15

```
Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
 50                  55                  60

Glu Gly Leu Ser Gly Asp Gln Met Gly Gln Ile Glu Lys Ile Phe Lys
 65                  70                  75                  80

Val Val Tyr Pro Val Asp Asp His His Phe Lys Val Ile Leu His Tyr
                 85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala
            165                 170
```

<210> SEQ ID NO 15
<211> LENGTH: 594
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(594)

<400> SEQUENCE: 15

```
atg gga gtc aaa gtt ctg ttt gcc ctg atc tgc atc gct gtg gcc gag      48
Met Gly Val Lys Val Leu Phe Ala Leu Ile Cys Ile Ala Val Ala Glu
 1               5                  10                  15 gcc aag ccc acc gaa ttc aag ctt ggt acc acc atg gtc ttc acc ctg      96
Ala Lys Pro Thr Glu Phe Lys Leu Gly Thr Thr Met Val Phe Thr Leu
            20                  25                  30 gag gac ttc gtc ggc gac tgg aga cag acc gcc ggc tac aac ctg gac     144
Glu Asp Phe Val Gly Asp Trp Arg Gln Thr Ala Gly Tyr Asn Leu Asp
        35                  40                  45 cag gtc ctg gag cag ggc ggc gtc agc agc ctg ttc cag aac ctg ggc     192
Gln Val Leu Glu Gln Gly Gly Val Ser Ser Leu Phe Gln Asn Leu Gly
 50                  55                  60 gtc agc gtc acc ccc atc cag aga atc gtc ctt agc ggc gag aac ggc     240
Val Ser Val Thr Pro Ile Gln Arg Ile Val Leu Ser Gly Glu Asn Gly
 65                  70                  75                  80 ctg aag atc gac atc cac gtc atc atc ccc tac gag ggc ctg agc ggc     288
Leu Lys Ile Asp Ile His Val Ile Ile Pro Tyr Glu Gly Leu Ser Gly
                 85                  90                  95 gac cag atg ggc cag atc gag aag atc ttc aag gtc gtc tac ccc gtc     336
Asp Gln Met Gly Gln Ile Glu Lys Ile Phe Lys Val Val Tyr Pro Val
            100                 105                 110 gac gac cac cac ttc aag gtc atc ctg cac tac ggc acc ctg gtc atc     384
Asp Asp His His Phe Lys Val Ile Leu His Tyr Gly Thr Leu Val Ile
        115                 120                 125 gac ggc gtc acc ccc aac atg atc gac tac ttc ggt aga ccc tac gag     432
Asp Gly Val Thr Pro Asn Met Ile Asp Tyr Phe Gly Arg Pro Tyr Glu
130                 135                 140
```

```
ggc atc gcc gtc ttc gac ggc aag aag atc acc gtc acc ggc acc ctg    480
Gly Ile Ala Val Phe Asp Gly Lys Lys Ile Thr Val Thr Gly Thr Leu
145                 150                 155                 160 tgg aac ggc aac aag atc atc gac gag aga ctg atc aac ccc gac ggc    528
Trp Asn Gly Asn Lys Ile Ile Asp Glu Arg Leu Ile Asn Pro Asp Gly
                165                 170                 175 agc ctg ctg ttc aga gtc acc atc aac ggc gtc acc ggc tgg aga ctg    576
Ser Leu Leu Phe Arg Val Thr Ile Asn Gly Val Thr Gly Trp Arg Leu
            180                 185                 190 tgc gag aga atc ctg gcc                                             594
Cys Glu Arg Ile Leu Ala
        195
```

<210> SEQ ID NO 16
<211> LENGTH: 198
<212> TYPE: PRT
<213> ORGANISM: Artificial sequence
<220> FEATURE:
<223> OTHER INFORMATION: Synthetic Construct

<400> SEQUENCE: 16

```
Met Gly Val Lys Val Leu Phe Ala Leu Ile Cys Ile Ala Val Ala Glu
1               5                   10                  15

Ala Lys Pro Thr Glu Phe Lys Leu Gly Thr Thr Met Val Phe Thr Leu
            20                  25                  30

Glu Asp Phe Val Gly Asp Trp Arg Gln Thr Ala Gly Tyr Asn Leu Asp
        35                  40                  45

Gln Val Leu Glu Gln Gly Gly Val Ser Ser Leu Phe Gln Asn Leu Gly
    50                  55                  60

Val Ser Val Thr Pro Ile Gln Arg Ile Val Leu Ser Gly Glu Asn Gly
65                  70                  75                  80

Leu Lys Ile Asp Ile His Val Ile Ile Pro Tyr Glu Gly Leu Ser Gly
                85                  90                  95

Asp Gln Met Gly Gln Ile Glu Lys Ile Phe Lys Val Val Tyr Pro Val
            100                 105                 110

Asp Asp His His Phe Lys Val Ile Leu His Tyr Gly Thr Leu Val Ile
        115                 120                 125

Asp Gly Val Thr Pro Asn Met Ile Asp Tyr Phe Gly Arg Pro Tyr Glu
    130                 135                 140

Gly Ile Ala Val Phe Asp Gly Lys Lys Ile Thr Val Thr Gly Thr Leu
145                 150                 155                 160

Trp Asn Gly Asn Lys Ile Ile Asp Glu Arg Leu Ile Asn Pro Asp Gly
                165                 170                 175

Ser Leu Leu Phe Arg Val Thr Ile Asn Gly Val Thr Gly Trp Arg Leu
            180                 185                 190

Cys Glu Arg Ile Leu Ala
        195
```

<210> SEQ ID NO 17
<211> LENGTH: 513
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(513)

<400> SEQUENCE: 17

```
atg gtc ttc acc ctg gag gac ttc gtc ggc gac tgg aga cag acc gcc      48
Met Val Phe Thr Leu Glu Asp Phe Val Gly Asp Trp Arg Gln Thr Ala
1               5                   10                  15 ggc tac aac ctg gac cag gtc ctg gag cag ggc ggc gtc agc agc ctg      96
Gly Tyr Asn Leu Asp Gln Val Leu Glu Gln Gly Gly Val Ser Ser Leu
            20                  25                  30 ttc cag aac ctg ggc gtc agc gtc acc ccc atc cag aga atc gtc ctt     144
Phe Gln Asn Leu Gly Val Ser Val Thr Pro Ile Gln Arg Ile Val Leu
        35                  40                  45 agc ggc gag aac ggc ctg aag atc gac atc cac gtc atc atc ccc tac     192
Ser Gly Glu Asn Gly Leu Lys Ile Asp Ile His Val Ile Ile Pro Tyr
    50                  55                  60 gag ggc ctg agc ggc gac cag atg ggc cag atc gag aag atc ttc aag     240
Glu Gly Leu Ser Gly Asp Gln Met Gly Gln Ile Glu Lys Ile Phe Lys
65                  70                  75                  80 gtc gtc tac ccc gtc gac gac cac cac ttc aag gtc atc ctg cac tac     288
Val Val Tyr Pro Val Asp Asp His His Phe Lys Val Ile Leu His Tyr
                85                  90                  95 ggc acc ctg gtc atc gac ggc gtc acc ccc aac atg atc gac tac ttc     336
Gly Thr Leu Val Ile Asp Gly Val Thr Pro Asn Met Ile Asp Tyr Phe
            100                 105                 110 ggt aga ccc tac gag ggc atc gcc gtc ttc gac ggc aag aag atc acc     384
Gly Arg Pro Tyr Glu Gly Ile Ala Val Phe Asp Gly Lys Lys Ile Thr
        115                 120                 125 gtc acc ggc acc ctg tgg aac ggc aac aag atc atc gac gag aga ctg     432
Val Thr Gly Thr Leu Trp Asn Gly Asn Lys Ile Ile Asp Glu Arg Leu
    130                 135                 140 atc aac ccc gac ggc agc ctg ctg ttc aga gtc acc atc aac ggc gtc     480
Ile Asn Pro Asp Gly Ser Leu Leu Phe Arg Val Thr Ile Asn Gly Val
145                 150                 155                 160 acc ggc tgg aga ctg tgc gag aga atc ctg gcc                         513
Thr Gly Trp Arg Leu Cys Glu Arg Ile Leu Ala
                165                 170

<210> SEQ ID NO 18
<211> LENGTH: 171
<212> TYPE: PRT
<213> ORGANISM: Artificial sequence
<220> FEATURE:
<223> OTHER INFORMATION: Synthetic Construct

<400> SEQUENCE: 18

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
```

```
                130                 135                 140
Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala
                165                 170
```

<210> SEQ ID NO 19
<211> LENGTH: 33
<212> TYPE: DNA
<213> ORGANISM: Artificial sequence
<220> FEATURE:
<223> OTHER INFORMATION: synthetic DNA

<400> SEQUENCE: 19
gcggaattct tcaccctgga ggacttcgtc ggc         33

<210> SEQ ID NO 20
<211> LENGTH: 36
<212> TYPE: DNA
<213> ORGANISM: Artificial sequence
<220> FEATURE:
<223> OTHER INFORMATION: synthetic DNA

<400> SEQUENCE: 20
gcctctagat taggccagga ttctctcgca cagtct         36

<210> SEQ ID NO 21
<211> LENGTH: 30
<212> TYPE: DNA
<213> ORGANISM: Artificial sequence
<220> FEATURE:
<223> OTHER INFORMATION: synthetic DNA

<400> SEQUENCE: 21
ggcgaattcg gtgggcttgg cctcggccac         30

<210> SEQ ID NO 22
<211> LENGTH: 20
<212> TYPE: DNA
<213> ORGANISM: Artificial sequence
<220> FEATURE:
<223> OTHER INFORMATION: synthetic DNA

<400> SEQUENCE: 22
taatacgact cactataggg         20

<210> SEQ ID NO 23
<211> LENGTH: 54
<212> TYPE: DNA
<213> ORGANISM: Artificial sequence
<220> FEATURE:
<223> OTHER INFORMATION: synthetic DNA

<400> SEQUENCE: 23
gccgaattca agcttggtac caccatggtc accctggagg acttcgtcgg cgac         54

<210> SEQ ID NO 24
<211> LENGTH: 54
<212> TYPE: DNA
<213> ORGANISM: Artificial sequence
<220> FEATURE:
<223> OTHER INFORMATION: synthetic DNA

<400> SEQUENCE: 24
gccgaattca agcttggtac caccatggtc ctggaggact tcgtcggcga ctgg         54

<210> SEQ ID NO 25
<211> LENGTH: 54
<212> TYPE: DNA
<213> ORGANISM: Artificial sequence
<220> FEATURE:
<223> OTHER INFORMATION: synthetic DNA

<400> SEQUENCE: 25
gccgaattca agcttggtac caccatggtc gaggacttcg tcggcgactg gaga        54

<210> SEQ ID NO 26
<211> LENGTH: 55
<212> TYPE: DNA
<213> ORGANISM: Artificial sequence
<220> FEATURE:
<223> OTHER INFORMATION: synthetic DNA

<400> SEQUENCE: 26
gccgaattca agcttggtac caccatggtc gacttcgtcg gcgactggag acaga       55

<210> SEQ ID NO 27
<211> LENGTH: 54
<212> TYPE: DNA
<213> ORGANISM: Artificial sequence
<220> FEATURE:
<223> OTHER INFORMATION: synthetic DNA

<400> SEQUENCE: 27
gccgaattca agcttggtac caccatggtc ttcgtcggcg actggagaca gacc        54

<210> SEQ ID NO 28
<211> LENGTH: 54
<212> TYPE: DNA
<213> ORGANISM: Artificial sequence
<220> FEATURE:
<223> OTHER INFORMATION: synthetic DNA

<400> SEQUENCE: 28
gccgaattca agcttggtac caccatggtc gtcggcgact ggagacagac cgcc        54

<210> SEQ ID NO 29
<211> LENGTH: 54
<212> TYPE: DNA
<213> ORGANISM: Artificial sequence
<220> FEATURE:
<223> OTHER INFORMATION: synthetic DNA

<400> SEQUENCE: 29
gccgaattca agcttggtac caccatggtc ggcgactgga gacagaccgc cggc        54

<210> SEQ ID NO 30
<211> LENGTH: 54
<212> TYPE: DNA
<213> ORGANISM: Artificial sequence
<220> FEATURE:
<223> OTHER INFORMATION: synthetic DNA

<400> SEQUENCE: 30
gccgaattca agcttggtac caccatggtc gactggagac agaccgccgg ctac        54

<210> SEQ ID NO 31
<211> LENGTH: 55
<212> TYPE: DNA
<213> ORGANISM: Artificial sequence
<220> FEATURE:

```
<223> OTHER INFORMATION: synthetic DNA

<400> SEQUENCE: 31
gccgaattca agcttggtac caccatggtc tggagacaga ccgccggcta caacc         55

<210> SEQ ID NO 32
<211> LENGTH: 55
<212> TYPE: DNA
<213> ORGANISM: Artificial sequence
<220> FEATURE:
<223> OTHER INFORMATION: synthetic DNA

<400> SEQUENCE: 32
gccgaattca agcttggtac caccatggtc ggctacaacc tggaccaggt cctgg         55

<210> SEQ ID NO 33
<211> LENGTH: 55
<212> TYPE: DNA
<213> ORGANISM: Artificial sequence
<220> FEATURE:
<223> OTHER INFORMATION: synthetic DNA

<400> SEQUENCE: 33
gccgaattca agcttggtac caccatggtc caggtcctgg agcagggcgg cgtca         55
```